US007842457B2

(12) United States Patent
Berka et al.

(10) Patent No.: US 7,842,457 B2
(45) Date of Patent: Nov. 30, 2010

(54) BEAD EMULSION NUCLEIC ACID AMPLIFICATION

(75) Inventors: Jan Berka, New Haven, CT (US); Yi-Ju Chen, New Haven, CT (US); John H. Leamon, Guilford, CT (US); Steve Lefkowitz, Branford, CT (US); Kenton L. Lohman, Guilford, CT (US); Vinod B. Makhijani, Guilford, CT (US); Jonathan M. Rothberg, Guilford, CT (US); Gary J. Sarkis, Guilford, CT (US); Maithreyan Srinivasan, Branford, CT (US); Michael P. Weiner, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 413 days.

(21) Appl. No.: 10/767,899

(22) Filed: Jan. 28, 2004

(65) Prior Publication Data

US 2005/0079510 A1   Apr. 14, 2005

Related U.S. Application Data

(60) Provisional application No. 60/443,471, filed on Jan. 29, 2003, provisional application No. 60/465,071, filed on Apr. 23, 2003, provisional application No. 60/476,313, filed on Jun. 6, 2003, provisional application No. 60/476,504, filed on Jun. 6, 2003, provisional application No. 60/476,592, filed on Jun. 6, 2003, provisional application No. 60/476,602, filed on Jun. 6, 2003, provisional application No. 60/497,985, filed on Aug. 25, 2003.

(51) Int. Cl.
*C12Q 1/68* (2006.01)
*C12P 19/34* (2006.01)

(52) U.S. Cl. .................... 435/6; 435/91.2

(58) Field of Classification Search ............ None
See application file for complete search history.

(56) References Cited

U.S. PATENT DOCUMENTS

| 4,801,529 | A | 1/1989 | Perlman et al. ............ 435/5 |
|---|---|---|---|
| 5,405,746 | A | 4/1995 | Uhlen ..................... 435/6 |
| 5,503,851 | A | 4/1996 | Mank et al. ............. 424/489 |
| 5,891,477 | A | 4/1999 | Lanza et al. ............ 424/501 |
| 5,989,892 | A | 11/1999 | Nishimaki et al. ...... 435/252.1 |
| 6,023,540 | A | 2/2000 | Walt et al. ............... 385/12 |
| 6,184,012 | B1 | 2/2001 | Neri et al. ............. 435/188 |
| 6,258,858 | B1 | 7/2001 | Nakajima et al. ........ 516/73 |
| 6,266,459 | B1 | 7/2001 | Walt et al. ............... 385/12 |
| 6,303,309 | B1* | 10/2001 | Jurinke et al. ............. 435/6 |
| 6,310,354 | B1 | 10/2001 | Hänninen et al. ...... 250/458.1 |
| 6,489,103 | B1 | 12/2002 | Griffiths et al. ............ 435/6 |
| 2001/0020011 | A1 | 9/2001 | Mathiowitz et al. ........ 514/44 |
| 2001/0036632 | A1* | 11/2001 | Yu et al. ................. 435/6 |
| 2002/0022038 | A1 | 2/2002 | Griffiths et al. ........... 435/6 |
| 2002/0119459 | A1 | 8/2002 | Griffiths ................. 435/6 |
| 2002/0155080 | A1 | 10/2002 | Glenn et al. ............ 424/70.5 |
| 2002/0172980 | A1 | 11/2002 | Phan et al. ............. 435/7.1 |
| 2003/0124586 | A1 | 7/2003 | Griffiths et al. ........... 435/6 |
| 2004/0005594 | A1 | 1/2004 | Holliger et al. ........... 435/6 |
| 2004/0053254 | A1* | 3/2004 | Wangh et al. ............. 435/6 |
| 2004/0253731 | A1 | 12/2004 | Holliger et al. ......... 435/458 |
| 2005/0037392 | A1 | 2/2005 | Griffiths et al. ........... 435/6 |
| 2005/0042648 | A1 | 2/2005 | Griffiths et al. ........... 435/6 |
| 2005/0064460 | A1 | 3/2005 | Holliger et al. ........... 435/6 |
| 2005/0069920 | A1 | 3/2005 | Griffiths et al. ........... 435/6 |
| 2005/0164239 | A1 | 7/2005 | Griffiths et al. ........... 435/6 |

FOREIGN PATENT DOCUMENTS

| DE | 196 46 372 C1 | 6/1997 |
|---|---|---|
| EP | 0 392 546 | 10/1990 |
| EP | 0 579 347 | 1/1994 |
| EP | 1 482 036 A2 | 12/2004 |
| EP | 1 522 581 | 4/2005 |
| EP | 1 522 582 | 4/2005 |
| EP | 1 594 980 | 11/2005 |
| WO | WO 89/10566 | 11/1989 |
| WO | WO 91/05058 | 4/1991 |
| WO | 93/03151 | 2/1993 |
| WO | WO 93/03151 A | 2/1993 |

(Continued)

OTHER PUBLICATIONS

Strizhkov et al. PCR amplification on a microarray of gel-immoblized oligonucleotides: detection of bacterial toxin- and drug-resistant genes and their mutations. BioTechniques (2000) vol. 29, No. 4, pp. 844-857).*

(Continued)

*Primary Examiner*—Kenneth R. Horlick
*Assistant Examiner*—David C Thomas
(74) *Attorney, Agent, or Firm*—Ivor R. Elrifi; Mintz Levin Cohn Ferris Glovsky and Popeo PC

(57) ABSTRACT

Disclosed are methods for nucleic acid amplification wherein nucleic acid templates, beads, and amplification reaction solution are emulsified and the nucleic acid templates are amplified to provide clonal copies of the nucleic acid templates attached to the beads. Also disclosed are kits and apparatuses for performing the methods of the invention.

20 Claims, 9 Drawing Sheets

FOREIGN PATENT DOCUMENTS

| | | |
|---|---|---|
| WO | WO 93/08278 A | 4/1993 |
| WO | WO 94/16332 | 7/1994 |
| WO | WO 94/23738 A | 10/1994 |
| WO | WO 94/24314 | 10/1994 |
| WO | WO 94/26766 | 11/1994 |
| WO | WO 95/11922 | 5/1995 |
| WO | WO 95/24929 A | 9/1995 |
| WO | WO 96/34112 A | 10/1996 |
| WO | WO 96/40723 | 12/1996 |
| WO | WO 97/40141 | 10/1997 |
| WO | WO 97/47763 | 12/1997 |
| WO | WO 98/13502 | 4/1998 |
| WO | WO 98/23733 | 6/1998 |
| WO | WO 98/31700 A | 7/1998 |
| WO | WO 98/34120 | 8/1998 |
| WO | WO 98/37186 | 8/1998 |
| WO | WO 98/41869 A | 9/1998 |
| WO | WO 99/02671 | 1/1999 |
| WO | WO 00/04139 | 1/2000 |
| WO | 00/40712 | 7/2000 |
| WO | WO 00/40712 | 7/2000 |
| WO | WO 01/18244 | 3/2001 |
| WO | WO 02/22869 | 3/2002 |
| WO | 02/103011 | 12/2002 |
| WO | WO 02/103363 | 12/2002 |
| WO | WO 03/044187 | 5/2003 |
| WO | WO 2004/069849 A2 | 8/2004 |
| WO | WO 2004/083443 A1 | 9/2004 |

OTHER PUBLICATIONS

Andreadis et al. Use of immobilized PCR primers to generate covalently immoblilized DNAs for in vitro transcription/translation reactions. Nucleic Acids Res. (2000) vol. 28, No. 2, e5, pp. i-viii.*
Bauer, Johann (1999). *J. Chromotography* 722: 55-69.
Brody & Quake (1999). *Applied Physics Letters* 74: 144-146.
Dressman et al. (2003). *PNAS* 100: 8817-8822.
Ghadessy et al. (2001). *PNAS* 99: 4552-4557.
Griffiths & Tawfik (2003). *EMBO J.* 22: 24-35.
Sepp et al. (2002). *FEBS Letters* 532: 455-458.
Tawfik & Griffiths (1998). *Nat Biotechnol* 16: 652-656.
Anarbaev, et al. (1998). Klenow Fragment and DNA Polymerase α-Primase Fromserva Calf Thymus in Water-in-Oil Microemulsions, *Biochimica et Biophysica Acta*, 1384:315-324.
Atwell et al. (1999). Selection for Improved Subtiligases by Phage Display, *Proc. Natl. Acad. Sci. USA*, 96:9497-9502.
Bass et al. (1990). Hormone Phage: An Enrichment Method for Variant Proteins with Altered Binding Properties, *Proteins: Structure, Function, and Genetics*, 8:309-314.
Chakrabarti, et al. (1994). Production of RNA by a Polymerase Protein Encapsulated Within Phospholipid Vesicles, *J. Mol. Evol.*, 39:555-559.
Chapman et al. (1994). In vitro Selection of Catalytic RNAs, *Structural Biology*, 4:618-622.
Clackson et al. (1994). In vitro Selection from Protein and Peptide Libraries, *Trends in Biotechnology*, 12:173-184.
Cull et al. (1992). Screening for Receptor Ligands Using Large Libraries of Peptides Linked to the C Terminus of the *lac* Repressor, *Proc. Natl. Acad. Sci. USA*, 89: 1865-1869.
Demartis et al. (1999). *A Strategy for the Isolation of Catalytic Activities from Repertoires of Enzymes Displayed on Phage*, Academic Press Limited, Article No. jmbi, 1998.2476, pp. 617-633.
Eigen (1976). Wie Entsteht Information? Prinzipien der Selbstorganisation in der Biologie, *Berichte der Bunsen-Gesellschaft Fur Physikalische Chemie*, 80(11):1059-1081.
Eigen et al. (1980). Hypercycles and Compartments. Compartments Assists-but do not replace-Hypercyclic Organization of Early Genetic Information, *J. Theor. Biol.*, 85:407-411.
Eigen et al. (1991). The Hypercycle. Coupling of RNA and Protein Biosynthesis in the Infection Cycle of an RNA Bacteriophage, *Biochemistry*, 30(40):11005-11018.

Ellington et al. (1990). In vitro Selection of RNA Molecules that Bind Specific Ligands, *Nature*, 346:818-822.
Gašperlin et al. (2000). Viscosity Prediction of Lipophilic Semisolid Emulsion Systems by Neural Modelling, *Int'l J. Pharm.*, 196:37-50.
Gašperlin et al. (1994). The Structure Elucidation of Semisolid w/o Emulsion Systems Containing Surfactant, *Int'l J. Pharm.*, 107:51-56.
Gold et al. (1995). Diversity of Oligonucleotide Functions, *Annu. Rev. Biochem.*, 64:763-797.
Green et al. (1992). Selection of a Ribozyme that Functions as a Superior Template in a Self-Copying Reaction, *Science*, 258:1910-1915.
Hanes et al. (1997). In vitro Selection and Evolution of Functional Proteins by Using Ribosome Display, *National Academy Science*, 94:4937-4942.
Hsu et al. (1999). Comparison of Process Parameters for Microencapsulation of Plasmid DNA in Poly(D,L-Lactic-co-Glycolic Acid Microspheres, *J. Drug Target*, 7:313-23.
Janda, et al. (1997). *Chemical Selection for Catalysis in Combinatorial Antibody Libraries*, www.sciencemag.org, 275:945-948.
Jestin et al. (1999). A Method for the Selection of Catalytic Activity Using Phage Display and Proximity Coupling, *Angew Chem. Int.*, 38:1124-1127, No. 8.
Joyce et al. (1994). In vitro Evolution of Nucleic Acids, *Structural Biology*, 4:331-336.
Keij et al. (1994) High-Speed Photodamage Cell Sorting: An Evaluation of the ZAPPER Prototype, *Methods in Cell Biology*, 42:371-386.
Mattheakis et al. (1994). An in vitro Polysome Display System for Identifying Ligands from Very Large Peptide Libraries, *Proc. Natl. Acad. Sci. USA*, 91:9022-9026.
McCafferty et al. (1990). Phage Antibodies: Filamentous Phage Displaying Antibody Variable Domains, *Nature*, 348:552-554.
Moore (1995). Exploration by Lamp Light, *Nature*, 374:766-767.
Nemoto et al. (1997). In vitro Virus: Bonding of mRNA bearing Puromycin at the 3'-Terminal End to the C-Terminal End of its Encoded Protein on the Ribosome in vitro, *Federation of European Biochemical Societies*, pp. 405-408.
Oberholzer et al. (1995). Enzymatic RNA Replication in Self-Reproducing Vesicles: An Approach to a Minimal Cell, *Biochemical and Biophysical Research Communications*, Academic Press, Inc., 207:250-257.
Oberholzer et al. (1995). Polymerase Chain Reaction in Liposomes, *Chemistry & Biology*, 2:677-682.
Pedersen et al. (1998). A Method for Directed Evolution and Functional Cloning of Enzymes, *Proc. Natl. Acad. Sci. USA*, 95:10523-10528.
Pelletier et al. (1999). An in vivo Library-versus Library Selection of Optimized Protein-Protein Interactions, *Nature Biotechnology*, 17:683-690.
Roberts et al. (1997). RNA-Peptide Fusions for the in vitro Selection of Peptides and Proteins, *Proc. Natl. Acad. Sci. USA*, 94:12297-12302.
Smith (1985). Filamentous Fusion Phage: Novel Expression Vectors that Display Cloned Antigens on the Virion Surface, *Science*, 228:1315-1317.
Soumillion (1994). Selection of β-Lactamase on Filamentous Bacteriophage by Catalytic Activity, *J. Mol. Biol.*, 237:415-422.
Suzuki et al. (1996). Random Mutagenesis of *Thermus aquaticus* DNA Polymerase I: Concordance of Immutable Sites in vivo with the Crystal Structure, *Proc. Natl. Acad. Sci. USA*, 93:9670-9675.
Tawfik et al. (1997). Efficient and Selective p -Nitrophenyl-Ester-Hydrolyzing Antibodies Elicited by a *p*-Nitrobenzyl Phosphonate Hapten, *European Journal of Biochemistry*, 244:619-626.
Tuerk et al. (1990). Systematic Evolution of Ligands by Exponential Enrichment: RNA Ligands to Bacteriophage T4 DNA Polymerase, *Science*, 249:505-510.
Vainshtein et al. (1996). Peptide Rescue of an N-Terminal Truncation of the Stoffel Fragment of *Taq* DNA Polymerase, *Protein Science*, 5:1785-1792.
Vogelstein et al. (1999). Digital PCR, *Proc. Natl. Acad. Sci. USA*, 96:9236-9241.

Walde et al. (1994). Oparin's Reactions Revisted: Enzymatic Synthesis of Poly(adenylic acid) in Micelles and Self-Reproducing Vesicles, *J. American Chemical Society*, 116:7541-7547.

Warburton (1993). Microcapsules from Multiple Emulsions, *Royal Society of Chemistry*, 138:35-51.

Wick (1996). Enzyme-Containing Liposomes Can Endogenously Produce Membrane-Constituting Lipids, *Chemistry & Biology*, 3:277-285.

Widersten et al. (1995). Glutathione Transferases with Novel Active Sites Isolated by Phage Display from a Library of Random Mutants, *J. Mol. Biol.*, 250:115-122.

Chiou et al. (2001). "A Closed-Cycle Capillary Polymerase Chain Reaction Machine", *Analytical Chemistry, American Chemical Society*, 73:2018-2021.

Katsura, et al. (2001). "Indirect Micromanipulation of Single Molecules in Water-in-Oil Emulsion", *Electrophoresis*, 22:289-293.

Kawakatsu et al. (1997). "Regular-Sized Cell Creation in Microchannel Emulsification by Visual Microprocessing Method", *Journal of the American Oil Chemists' Society*, 74:317-321.

Kopp et al. (1998). "Chemical Amplification: Continuous Flow PCR on a Chip", *Science, American Association for the Advancement of Science*, 280:1046-1048.

Lund, et al. (1988). "Assesment of Methods for Covalent Binding of Nucleic Acids to Magnetic Beads, Dynabeads™, and the Characteristics of the Bound Nucleic Acids in Hybridization Reactions", *Nucleic Acids Research*, Oxford University Press, 16, No. 22, 20 pgs.

Lundeberg et al. (1995). "Solid-Phase Technology: Magnetic Beads to Improve Nucleic Acid Detection and Analysis", *Biotechnology Annual Review*, 1:373-401.

Nakano et al. (1994). "High Speed Polymerase Chain Reaction in Constant Flow", *Bioscience Biotechnology and Biochemistry*, 58:349-352.

Nakano et al. (2003). "Single-Molecule PCR Using Water-in-Oil Emulsion", *Journal of Biotechnology*, 102:117-124.

Park et al. (2003). "Cylindrical Compact Thermal-Cycling Device for Continuous-Flow Polymerase Chain Reaction", *Analytical Chemistry, American Chemical Society*, 75:6029-6033.

Russom et al. (2003). "Single-Nucleotide Polymorphism Analysis by Allele-Specific Extension of Fluorescently Labeled Nucleotides in a Microfluidic Flow-Through Device", *Electrophoresis*, 24:158-161.

Schneegass et al. (2001). "Miniaturized Flow-Through PCR With Different Template Types in a Silicone Chip Thermocycler", *Lab on a Chip, Royal Society of Chemistry*, 1:42-49.

Ruzicka (2000), Analyst, 125:1053-1060.

Andreadis et al. (2000), Nucleic Acids Research, 28:i-viii.

Bruckner-Lea et al. (2001), Analytica Chimica Acta, 21616:1-12.

Bruno et al. (1996), Journal of Molecular Recognition, 9:474-479.

Fan et al. (1999), Analytical Chemistry, 71:4851-4859.

Nisisako et al. (2003), IEEE, 0-7803-7744-3/03.

Obeid et al. (2003), Analytical Chemistry, 75:288-295.

Schneegass et al. (2001), Reviews in Molecular Biotechnology, 82:101-121.

Andreadis et al. (2000), Nucleic Acids Research, 28:i-viii.

Erlich, Henry A., Editor (1989) PCR Technology, Chapter 5, pp. 50-53.

Dressman et al. (2003), PNAS, 100:8817-8822.

Drmanc et al. (1990), Scientia Yugoslavica, 16:97-107.

Fry et al. (1992), BioTechniques, 13:124.

Hultman et al. (1989), Nucleic Acids Research, 17:4937-4946.

Yang et al. (1998), Chemistry Letters, 257-258.

Claims Listing from EP 1 522 582 B1.

Notice of Opposition to a European Patent (EP1594980) dated Aug. 9, 2010 (30 pages).

* cited by examiner

SEQUENCE LISTING

```
<160> NUMBER OF SEQ ID NOS: 7

<210> SEQ ID NO 1
<211> LENGTH: 40
<212> TYPE: DNA
<213> ORGANISM: Artificial
<220> FEATURE:
<223> OTHER INFORMATION: Oligonucleotide

<400> SEQUENCE: 1
gcttacctga ccgacctctg cctatcccct gttgcgtgtc                                40

<210> SEQ ID NO 2
<211> LENGTH: 40
<212> TYPE: DNA
<213> ORGANISM: Artificial
<220> FEATURE:
<223> OTHER INFORMATION: Oligonucleotide

<400> SEQUENCE: 2
ccattcccca gctcgtcttg ccatctgttc cctccctgtc                                40

<210> SEQ ID NO 3
<211> LENGTH: 20
<212> TYPE: DNA
<213> ORGANISM: Artificial
<220> FEATURE:
<223> OTHER INFORMATION: Oligonucleotide

<400> SEQUENCE: 3
gcttacctga ccgacctctg                                                      20

<210> SEQ ID NO 4
<211> LENGTH: 20
<212> TYPE: DNA
<213> ORGANISM: Artificial
<220> FEATURE:
<223> OTHER INFORMATION: Oligonucleotide

<400> SEQUENCE: 4
ccattcccca gctcgtcttg                                                      20

<210> SEQ ID NO 5
<211> LENGTH: 44
<212> TYPE: DNA
<213> ORGANISM: Artificial
<220> FEATURE:
<223> OTHER INFORMATION: Oligonucleotide

<400> SEQUENCE: 5
ccattcccca gctcgtcttg ccatctgttc cctccctgtc tcag                           44

<210> SEQ ID NO 6
<211> LENGTH: 20
<212> TYPE: DNA
```

-continued

```
<213> ORGANISM: Artificial
<220> FEATURE:
<223> OTHER INFORMATION: Oligonucleotide

<400> SEQUENCE: 6
ccatctgttc cctccctgtc                                            20

<210> SEQ ID NO 7
<211> LENGTH: 20
<212> TYPE: DNA
<213> ORGANISM: Artificial
<220> FEATURE:
<223> OTHER INFORMATION: Oligonucleotide

<400> SEQUENCE: 7
cctatcccct gttgcgtgtc                                            20
```

US 7,842,457 B2

BEAD EMULSION NUCLEIC ACID AMPLIFICATION

RELATED APPLICATIONS

This application claims the benefit of priority to the following applications: U.S. Ser. No. 60/443,471 filed Jan. 29, 2003, U.S. Ser. No. 60/465,071 filed Apr. 23, 2003; U.S. Ser. No. 60/476,313 filed on Jun. 6, 2003, U.S. Ser. No. 60/476,504 filed Jun. 6, 2003, U.S. Ser. No. 60/476,592 filed on Jun. 6, 2003; U.S. Ser. No. 60/476,602 filed on Jun. 6, 2003, and U.S. Ser. No. 60/497,985 filed Aug. 25, 2003. All patent and patent applications in this paragraph are hereby fully incorporated herein by reference.

This application also incorporates by reference the following copending U.S. patent applications: "Method For Preparing Single-Stranded DNA Libraries" filed Jan. 28, 2004, "Double Ended Sequencing" filed Jan. 28, 2004, and "Methods Of Amplifying And Sequencing Nucleic Acids" filed Jan. 28, 2004.

FIELD OF THE INVENTION

The present invention relates to methods for amplifying nucleic acid templates from low copy number to quantities amenable for sequencing on a solid support such as a bead. The present invention is also directed to zero bead removal—a method of enriching for solid support containing amplified nucleic acids is also disclosed.

BACKGROUND

The ability to amplify a plurality of nucleic acid sequences, such as a genomic library or a cDNA library, is critical given the inefficiency of current methods of sequencing. Current sequencing technologies require millions of copies of nucleic acid per sequencing reaction. Furthermore, the sequencing of a human genome would require about tens of millions of different sequencing reactions. If the starting material is limited, amplification of the initial DNA is necessary before genomic sequencing. The starting material may be limited, for example, if the genome to be sequenced is from a trace quantity of pathogen or from a prenatal patient. Current techniques for in vitro genome amplification involve laborious cloning and culturing protocols that have limited the utility of genomic sequencing. Other techniques, such as PCR, while fast and reliable, are unable to amplify a genome in a representative fashion.

While random primed PCR can be easily engineered to amplify a plurality of nucleic acids in one reaction, this method is not preferred because the amplified library is not representative of the starting library. That is, in a random PCR environment, some DNA sequences are preferentially amplified at the expense of other sequences such that the amplified product does not represent the starting material. This problem with PCR may be overcome if each individual member of a library is amplified in a separate reaction. However, this approach may be impractical if many thousands of separate reaction tubes are required for the amplification process, as a genomic library or cDNA library may include more than 100,000 fragments. Individual amplification of each fragment of these libraries in separate reaction is not practical.

SUMMARY OF THE INVENTION

The present invention provides for a method of amplifying a plurality of nucleic acids (e.g., each sequence of a DNA library, transcriptome, or genome) in a rapid and economical manner in a single reaction tube. One use of the method of the invention is to perform simultaneous clonal amplification (e.g., by PCR) of a plurality of samples (as many as several hundred thousand) in one reaction vessel. This invention further provides means for encapsulating a plurality of DNA samples individually in a microcapsule of an emulsion (i.e., a microreactor), performing amplification of the plurality of encapsulated nucleic acid samples simultaneously, and releasing said amplified plurality of DNA from the microcapsules for subsequent reactions.

In one embodiment, single copies of the nucleic acid template species are hybridized to capture beads comprising, e.g., capture oligonucleotides or chemical groups that bind to the nucleic acid template. The beads are suspended in complete amplification solution (see Example 2 for an example of an amplification solution) and emulsified to produce microreactors (typically 100 to 200 microns in diameter). After this, amplification (e.g., PCR) is used to clonally increase copy number of the initial template species in the microreactors, and these copies bind to the capture beads in the microreactors.

In an alternate embodiment, capture beads are added to an amplification reaction mixture (e.g., an amplification solution from Example 2) comprising nucleic acid template and this mixture is emulsified to produce microreactors. Amplification (e.g., PCR) is used to clonally increase copy number of the initial template species in the microreactors, and these copies bind to the capture beads in the microreactors.

One advantage of the present invention is that the microreactors allow the simultaneous clonal and discrete amplification of many different templates without cross contamination of the amplified products or reagents, or domination of one particular template or set of templates (e.g., PCR bias). The amplification reaction, for example, may be performed simultaneously with at least 3,000 microreactors per microliter of reaction mix. Preferably, each microreactor comprises one or fewer species of amplified template.

In various embodiments of the invention, the microreactors have an average size of about 10 μm to about 250 μm. In a preferred embodiment, the microreactors have an average diameter of about 60 to about 200 μm. In a more preferred embodiment, the microreactors have an average diameter of about 60 μm, such as an average of 40 μm to 80 μm in diameter. In an embodiment, the microreactors have an average diameter of about 60 μm. In another preferred embodiment, the microreactors have an average volume of about 113 pl. In a most preferred embodiment, about 3000 microreactors are contained within a microliter of a 1:2 water to oil emulsion.

The present invention also provides for a method for producing a plurality of nucleic acid template-carrying beads wherein each bead comprises up to and more than 1,000,000 copies of a single nucleic acid sequence. In one preferred embodiment, each bead may comprise over 20 million copies of a single nucleic acid.

The present invention further provides for a library made by the methods of the invention. The library may be made by using, e.g., a genomic DNA library, a cDNA library, or a plasmid library as the starting material for amplification. The library may be derived from any population of nucleic acids, e.g., biological or synthetic in origin.

The present invention also provides for a method of enriching for those beads that contains the product of successful DNA amplification (i.e., by removing beads that have no DNA attached thereto).

DETAILED DESCRIPTION OF INVENTION

Brief Overview of Bead Emulsion Amplification

A brief overview of one embodiment of the invention is discussed below. A more detailed description of each individual step of this embodiment will follow. In this embodiment, PCR is the chosen amplification technique.

Figure 1:
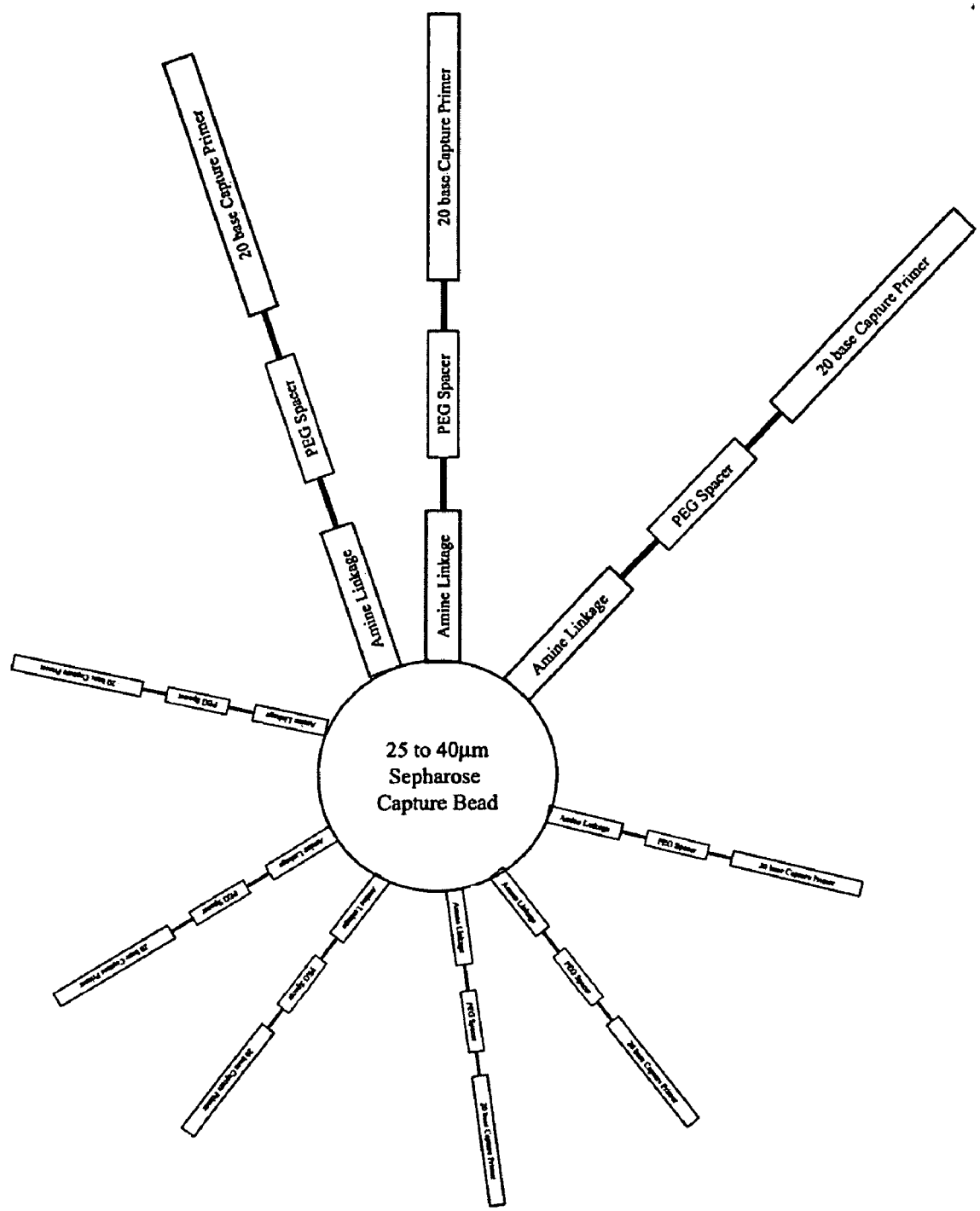
FIG. 1 Schematic of the structure of a DNA capture bead.
Figure 2A:
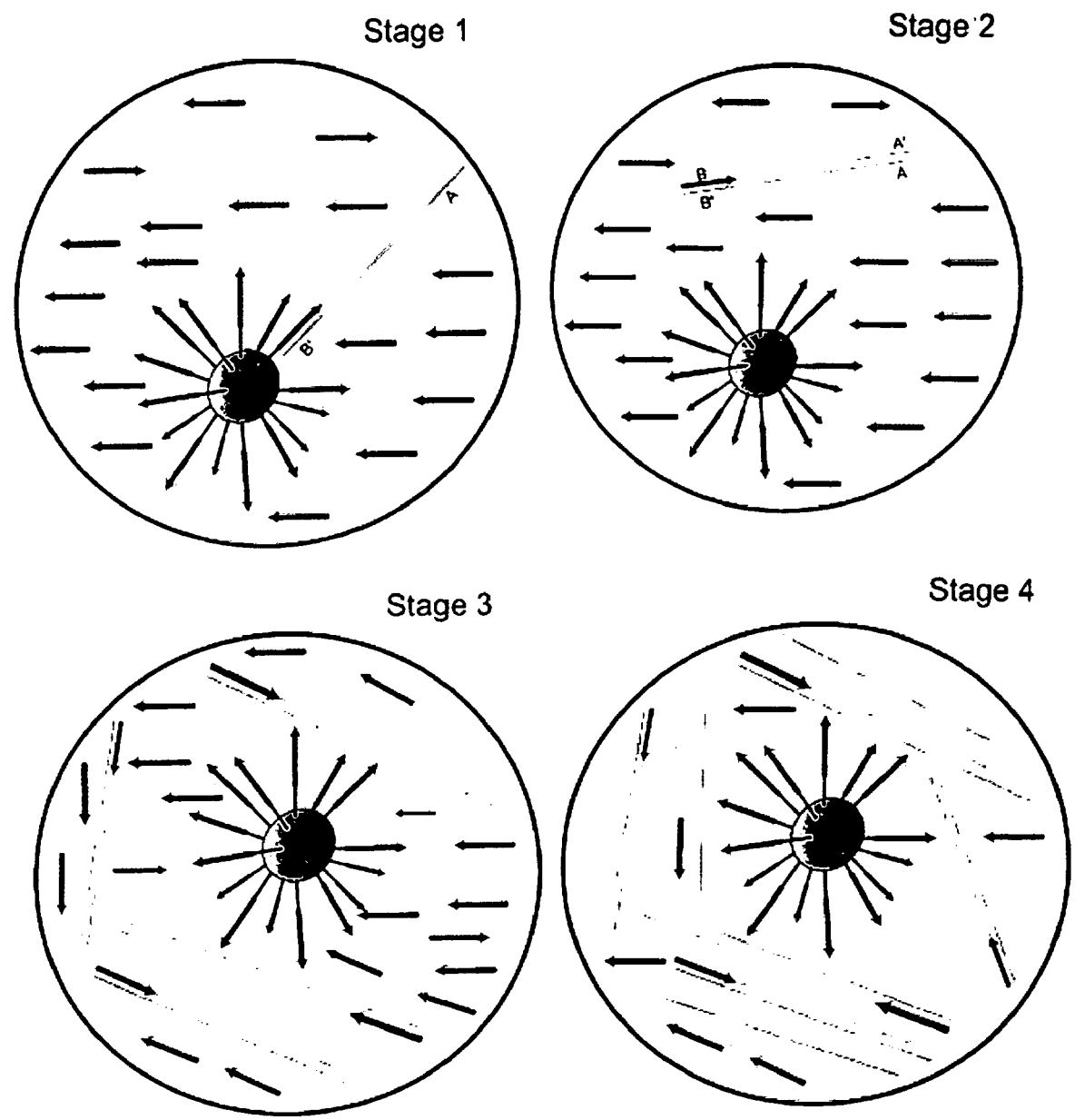
FIGS. 2A-2B Schematic of one embodiment of a bead emulsion amplification process.
Figure 2B:
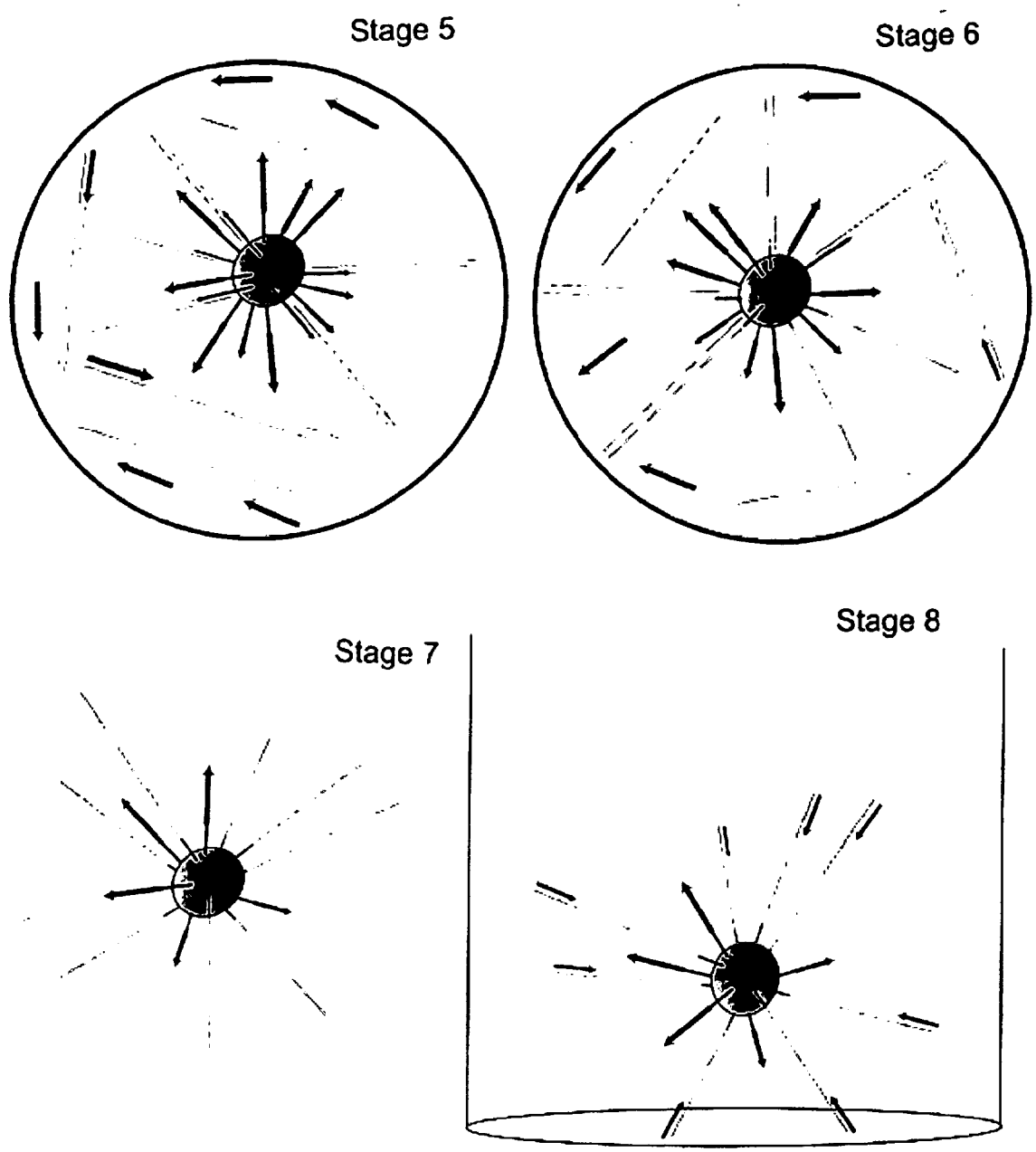

In one aspect of the invention, bead emulsion amplification is performed by attaching a template (e.g., DNA template) to be amplified to a solid support, preferably in the form of a generally spherical bead. The bead is linked to a large number of a single primer species (i.e., primer B in FIG. 2) that is complementary to a region of the template DNA and the amplification copies of this template. Alternately, the bead is linked to chemical groups (e.g., biotin) that can bind to chemical groups (e.g., streptavidin) included on the template DNA and amplification copies of this template. The beads are suspended in aqueous reaction mixture and then encapsulated in a water-in-oil emulsion. In different aspects of the invention, the template DNA is bound to the bead prior to emulsification, or the template DNA is included in solution in the amplification reaction mixture. In a preferred embodiment, an amplification step is performed prior to distribution of the nucleic acid templates onto a multiwell (e.g., picotiter) plate.

In certain embodiments, the emulsion is composed of discrete aqueous phase microdroplets, e.g., averaging approximately 60 to 200 µm in diameter, enclosed by a thermostable oil phase. Each microdroplet contains, preferably, amplification reaction solution (i.e., the reagents necessary for nucleic acid amplification). An example of an amplification reaction solution would be a PCR reaction mixture (polymerase, salts, dNTPs; see Example 2 for an example of one embodiment) and a pair of PCR primers (primer A and primer B). See, FIG. 2A. In some cases, the template DNA is included in the reaction mixture. A subset of the microdroplet population includes the DNA bead and the template. This subset of microdroplet is the basis for the amplification. The remaining microcapsules do not contain template DNA and will not participate in amplification. In one embodiment, the amplification technique is PCR and the PCR primers are present in an 8:1 or 16:1 ratio (i.e., 8 or 16 of one primer to 1 of the second primer) to perform asymmetric PCR. In another embodiment, the ratio of PCR primers may be substantially equal for normal PCR.

The amplification reaction, such as PCR, may be performedusing any suitable method. In the following overview, one mechanism of PCR is discussed as an illustration. However, it is understood that the invention is not limited to this mechanism. In the example, a region of the DNA molecule (B' region) is annealed to an oligonucleotide immobilized to a bead (primer B). During thermocycling (FIG. 2B), the bond between the single stranded template and the immobilized B primer on the bead is broken, releasing the template into the surrounding microencapsulated solution. The amplification solution, in this case, the PCR solution, contains addition solution phase primer A and primer B (e.g., in a 8:1 or 16:1 ratio). Solution phase B primers readily bind to the complementary B' region of the template as binding kinetics are more rapid for solution phase primers than for immobilized primers.

In early phase PCR, both A and B strands amplify equally well (FIG. 2C). By midphase PCR (i.e., between cycles 10 and 30) the B primers are depleted, halting exponential amplification. The reaction then enters asymmetric amplification and the amplicon population becomes dominated by A strands (FIG. 2D). In late phase PCR (FIG. 2E), after 30 to 40 cycles, asymmetric amplification increases the concentration of A strands in solution. Excess A strands begin to anneal to bead immobilized B primers. Thermostable polymerases then utilize the A strand as a template to synthesize an immobilized, bead bound B strand of the amplicon.

In final phase PCR (FIG. 2F), continued thermal cycling forces additional annealing to bead bound primers. Solution phase amplification may be minimal at this stage but concentration of immobilized B strands increase. Then, the emulsion is broken and the immobilized product is rendered single stranded by denaturing (by heat, pH etc.) which removes the complimentary A strand. The A primers are annealed to the A' region of immobilized strand, and immobilized strand is loaded with sequencing enzymes, and any necessary accessory proteins. The beads are then sequenced using recognized pyrophosphate techniques (described, e.g., in U.S. Pat. Nos. 6,274,320, 6258,568 and 6,210,891, incorporated in toto herein by reference).

Template Design

In a preferred embodiment, the nucleic acid template to be amplified by bead emulsion amplification is a population of DNA such as, for example, a genomic DNA library or a cDNA library. It is preferred that each member of the DNA population have a common nucleic acid sequence at the first end and a common nucleic acid sequence at a second end. This can be accomplished, for example, by ligating a first adaptor DNA sequence to one end and a second adaptor DNA sequence to a second end of each member of the DNA population. Many DNA and cDNA libraries, by nature of the cloning vector (e.g., Bluescript, Stratagene, La Jolla, Calif.) fit this description of having a common sequence at a first end and a second common sequence at a second end of each member DNA. The nucleic acid template may be of any size amenable to in vitro amplification (including the preferred amplification techniques of PCR and asymmetric PCR). In a preferred embodiment, the template is about 150 to 750 bp in size, such as, for example about 250 bp in size.

Binding Nucleic Acid Template to Capture Beads

In one aspect of the invention, a single stranded nucleic acid template to be amplified is attached to a capture bead. The template may be captured to the bead prior to emulsification or after the emulsion has been formed. In a preferred aspect, the amplification copies of the nucleic acid template are attached to a capture bead. As non-limiting examples, these attachments may be mediated by chemical groups or oligonucleotides that are bound to the surface of the bead. The nucleic acid (e.g., the nucleic acid template, amplification copies, or oligonucleotides) may be attached to the solid support (e.g., a capture bead) in any manner known in the art.

According to the present invention, covalent chemical attachment of a nucleic acid to the bead can be accomplished by using standard coupling agents. For example, water-soluble carbodiimide can be used to link the 5'-phosphate of a DNA sequence to amine-coated capture beads through a phosphoamidate bond. Alternatively, specific oligonucleotides can be coupled to the bead using similar chemistry, and to then DNA ligase can be used to ligate the DNA template to the oligonucleotide on the bead. Other linkage chemistries to join the oligonucleotide to the beads include the use of N-hydroxysuccinamide (NHS) and its derivatives.

In an exemplary method, one end of a linker may contain a reactive group (such as an amide group) which forms a covalent bond with the solid support, while the other end of the linker contains a second reactive group that can bond with the oligonucleotide to be immobilized. In a preferred embodiment, the oligonucleotide is bound to the DNA capture bead by covalent linkage. However, non-covalent linkages, such as chelation or antigen-antibody complexes, may also be used to join the oligonucleotide to the bead.

As non-limiting examples, oligonucleotides can be employed which specifically hybridize to unique sequences at the end of the DNA fragment, such as the overlapping end from a restriction enzyme site or the "sticky ends" of cloning vectors, but blunt-end linkers can also be used. These methods are described in detail in U.S. Pat. No. 5,674,743. It is preferred that the beads will continue to bind the immobilized oligonucleotide throughout the steps in the methods of the invention.

In one embodiment of the invention, each capture bead is designed to have a plurality of oligonucleotides that recognize (i.e., are complementary to) a portion of the nucleic template, and the amplification copies of this template. In the methods described herein, clonal amplification of the template species is desired, so it is preferred that only one unique nucleic acid species is attached to any one capture bead.

The beads used herein may be of any convenient size and fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, copolymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase supports known to those of skill in the art. In preferred embodiments, the capture beads are beads approximately 2 to 100 μm in diameter, or 10 to 80 μm in diameter, most preferably 20 to 40 μm in diameter. In a preferred embodiment, the capture beads are Sepharose beads.

Emulsification

For use with the present invention, capture beads with or without attached nucleic acid template are suspended in a heat stable water-in-oil emulsion. It is contemplated that a plurality of the microreactors include only one template and one bead. There may be many droplets that do not contain a template or which do not contain a bead. Likewise there may be droplets that contain more than one copy of a template. The emulsion may be formed according to any suitable method known in the art. One method of creating emulsion is described below but any method for making an emulsion may be used. These methods are known in the art and include adjuvant methods, counter-flow methods, cross-current methods, rotating drum methods, and membrane methods. Furthermore, the size of the microcapsules may be adjusted by varying the flow rate and speed of the components. For example, in dropwise addition, the size of the drops and the total time of delivery may be varied. Preferably, the emulsion contains a density of about 3,000 beads encapsulated per microliter.

Various emulsions that are suitable for biologic reactions are referred to in Griffiths and Tawfik, EMBO, 22, pp. 24-35 (2003); Ghadessy et al., Proc. Natl. Acad. Sci. USA 98, pp. 4552-4557 (2001); U.S. Pat. No. 6,489,103 and WO 02/22869, each fully incorporated herein by reference. It is noted that Griffiths et al., (U.S. Pat. No. 6,489,103 and WO 99/02671) refers to a method for in vitro sorting of one or more genetic elements encoding a gene products having a desired activity. This method involves compartmentalizing a gene, expressing the gene, and sorting the compartmentalized gene based on the expressed product. In contrast to the present invention, the microencapsulated sorting method of Griffith is not suitable for parallel analysis of multiple microcapsules because their nucleic acid product is not anchored and cannot be anchored. Since the nucleic acids of Griffiths are not anchored, they would be mixed together during demulsification.

The emulsion is preferably generated by adding beads to an amplification solution. As used herein, the term "amplification solution" means the sufficient mixture of reagents that is necessary to perform amplification of template DNA. One example of an amplification solution, a PCR amplification solution, is provided in the Examples below. It will be appreciated that various modifications may be made to the amplification solution based on the type of amplification being performed and whether the template DNA is attached to the beads or provided in solution. In one embodiment, the mixture of beads and amplification solution is added dropwise into a spinning mixture of biocompatible oil (e.g., light mineral oil, Sigma) and allowed to emulsify. In another embodiment, the beads and amplification solution are added dropwise into a cross-flow of biocompatible oil. The oil used may be supplemented with one or more biocompatible emulsion stabilizers. These emulsion stabilizers may include Atlox 4912, Span 80, and other recognized and commercially available suitable stabilizers. In preferred aspects, the emulsion is heat stable to allow thermal cycling, e.g., to at least 94° C., at least 95° C., or at least 96° C. Preferably, the droplets formed range in size from about 5 microns to about 500 microns, more preferably from about 10 microns to about 350 microns, even more preferably from about 50 to 250 microns, and most preferably from about 100 microns to about 200 microns. Advantageously, cross-flow fluid mixing allows for control of the droplet formation, and uniformity of droplet size. We note that smaller water droplets not containing beads may be present in the emulsion.

The microreactors should be sufficiently large to encompass sufficient amplification reagents for the degree of amplification required. However, the microreactors should be sufficiently small so that a population of microreactors, each containing a member of a DNA library, can be amplified by conventional laboratory equipment, e.g., PCR thermocycling equipment, test tubes, incubators and the like. Notably, the use of microreactors allows amplification of complex mixtures of templates (e.g., genomic DNA samples or whole cell RNA) without intermixing of sequences, or domination by one or more templates (e.g., PCR selection bias; see, Wagner et al., 1994, Suzuki and Giovannoni, 1996; Chandler et al., 1997, Polz and Cavanaugh, 1998).

With the limitations described above, the optimal size of a microreactor may be on average 100 to 200 microns in diameter. Microreactors of this size would allow amplification of a DNA library comprising about 600,000 members in a suspension of microreactors of less than 10 ml in volume. For example, if PCR is the chosen amplification method, 10 ml of microreactors would fit into 96 tubes of a regular thermocycler with 96 tube capacity. In a preferred embodiment, the suspension of 600,000 microreactors would have a volume of less than 1 ml. A suspension of less than 1 ml may be amplified in about 10 tubes of a conventional PCR thermocycler. In a most preferred embodiment, the suspension of 600,000 microreactors would have a volume of less than 0.5 ml.

Another embodiment of the invention is directed to a method of performing nucleic acid amplification with a template and a bead, but without attachment of the template to the bead. In one aspect, the bead may comprise a linker molecule that can bind the amplified nucleic acid after amplification. For example, the linker may be a linker that can be activated. Such linkers are well known and include temperature sensitive or salt sensitive binding pairs such as streptavidin/biotin and antibodies/antigen. The template nucleic acid may be encapsulated with a bead and amplified. Following amplification, the amplified nucleic acid may be linked to the beads, e.g., by adjustments in temperature or salt concentration.

Amplification

After encapsulation, the template nucleic acid may be amplified, while attached or unattached to beads, by any suitable method of amplification including transcription-based amplification systems (Kwoh D. et al., Proc. Natl. Acad Sci. (U.S.A.) 86:1173 (1989); Gingeras T. R. et al., WO 88/10315; Davey, C. et al., EP Publication No. 329,822; Miller, H. I. et al., WO 89/06700), "RACE" (Frohman, M. A., In: PCR Protocols: A Guide to Methods and Applications, Academic Press, NY (1990)) and one-sided PCR (Ohara, O. et al., Proc. Natl. Acad. Sci. (U.S.A.) 86.5673-5677 (1989)). Still other methods such as di-oligonucleotide amplification, isothermal amplification (Walker, G. T. et al., Proc. Natl. Acad. Sci. (U.S.A.) 89:392-396 (1992)), Nucleic Acid Sequence Based Amplification (NASBA; see, e.g., Deiman B et al., 2002, Mol Biotechnol. 20(2):163-79), whole-genome amplification (see, e.g., Hawkins T L et al., 2002, Curr Opin Biotechnol. 13(1):65-7), strand-displacement amplification (see, e.g., Andras S C, 2001, Mol Biotechnol. 19(1):29-44), rolling circle amplification (reviewed in U.S. Pat. No. 5,714, 320), and other well known techniques may be used in accordance with the present invention.

In a preferred embodiment, DNA amplification is performed by PCR. PCR according to the present invention may be performed by encapsulating the target nucleic acid with a PCR solution comprising all the necessary reagents for PCR. Then, PCR may be accomplished by exposing the emulsion to any suitable thermocycling regimen known in the art. In a preferred embodiment, 30 to 50 cycles, preferably about 40 cycles, of amplification are performed. It is desirable, but not necessary, that following the amplification procedure there be one or more hybridization and extension cycles following the cycles of amplification. In a preferred embodiment, 10 to 30 cycles, preferably about 25 cycles, of hybridization and extension are performed (e.g., as described in the examples). Routinely, the template DNA is amplified until typically at least 10,000 to 50,000,000 copies are immobilized on each bead. It is recognized that for nucleic acid detection applications, fewer copies of template are required. For nucleic acid sequencing applications we prefer that at least two million to fifty million copies, preferably about ten million to thirty million copies of the template DNA are immobilized on each bead. The skilled artisan will recognize that the size of bead (and capture site thereon) determines how many captive primers can be bound (and thus how many amplified templates may be captured onto each bead).

PCR Primer Design

The selection of nucleic acid primers for amplification, such as PCR amplification, is well within the abilities of one of skill in the art. Strategies for primer design may be found throughout the scientific literature, for example, in Rubin, E. and A. A. Levy, Nucleic Acids Res, 1996. 24(18): p. 3538-45; and Buck, G. A., et al., Biotechniques, 1999. 27(3): p. 528-36. In a preferred embodiment, primers can be limited to a length of 20 bases (5 tetramers) for efficient synthesis of bipartite PCR/sequencing primers. Each primer can include a two-base GC clamp on the 5' end, a single GC clamp on the 3' end, and all primers can share similar $T_m$ (±2° C.). In a preferred embodiment, hairpin structures within the primers (internal hairpin stems $\Delta G > -1.9$ kcal/mol) are strongly discouraged in any of the designed primers. In another preferred embodiment, primer dimerization is also controlled; such that a 3-base maximum acceptable dimer is allowed. However, this is allowed to occur only in the final six 3' bases, and the maximum allowable $\Delta G$ for a 3' dimer is −2.0 kcal/mol. Preferably, a penalty is applied to primers in which the 3' ends are too similar to others in the group. This prevents cross-hybridization between one primer and the reverse complement of another primer.

If the primers are designed according to the criteria described above, the possibility of complimentary regions occurring within the genome of interest is not of major concern, despite the reported tolerance of PCR to mismatches in complex sample populations (Rubin, E. and A. A. Levy. Nucleic Acids Res, 1996. 24(18): p. 3538-45). Although the probability of finding a perfect match to a 20 base primer is extremely low ($4^{20}$) (see Table 1), the probability of finding shorter non-consecutive matches increases significantly with the size of the genome of interest. As a result, the probability of finding a perfect match for a sequence of at least 10 of 20 bases is 99.35% for an Adenovirus genome. The probability of finding a perfect match for a sequence of 16 bases is 97% for the sequences in the NCBI database (approximately 100 times more sequence information than the Adenovirus genome). The probability of finding a perfect match for a sequence of 17 to 20 bases is 99% for the human genome (approximately 3 billion bases).

TABLE 1

The probability of perfect sequence matches for primers increases with decreasing match length requirements and increasing size of the genome of interest.

| Match Length | Perfect match probability ($1/(4^{length})$) | % chance for match in Adeno ~35 K bases | % chance for match in NCBI bacterial database ~488 M bases | % chance for match in Human ~3 B bases |
|---|---|---|---|---|
| 20 | 9.1E−13 | 0.00% | 0.04% | 0.27% |
| 19 | 7.3E−12 | 0.00% | 0.65% | 4.32% |
| 18 | 4.4E−11 | 0.00% | 5.76% | 34.37% |
| 17 | 2.3E−10 | 0.00% | 35.69% | 99.17% |
| 16 | 1.2E−09 | 0.02% | 97.52% | >100% |
| 15 | 5.6E−09 | 0.12% | >100% | >100% |
| 14 | 2.6E−08 | 0.64% | >100% | >100% |
| 13 | 1.2E−07 | 3.29% | >100% | >100% |
| 12 | 5.4E−07 | 15.68% | >100% | >100% |
| 11 | 2.4E−06 | 58.16% | >100% | >100% |
| 10 | 1.0E−05 | 99.35% | >100% | >100% |
| 9 | 4.6E−05 | 99.77% | >100% | >100% |
| 8 | 2.0E−04 | >100% | >100% | >100% |
| 7 | 8.5E−04 | >100% | >100% | >100% |
| 6 | 3.7E−03 | >100% | >100% | >100% |
| 5 | 1.6E−02 | >100% | >100% | >100% |
| 4 | 6.4E−02 | >100% | >100% | >100% |
| 3 | 2.5E−01 | >100% | >100% | >100% |
| 2 | 7.1E−01 | >100% | >100% | >100% |
| 1 | 1.0E+00 | >100% | >100% | >100% |

However, primer cross-hybridization to various regions of the genome is less problematic than one might expect due to the random DNA digestion used to form the nucleic acid templates. The cross-hybridizing regions (CHRs) are fairly benign. First, it is unlikely that a CHR would be able to successfully compete with the perfect match between the PCR primers in solution and the template. In addition, any primers that include mismatches at their 3' end will be at a significant competitive disadvantage. Even if a CHR should out compete the intended PCR primer, it would produce a truncated PCR product, without a downstream site for the sequencing primer. If the truncated product could be driven to the capture bead and immobilized, one of two situations would result. If the CHR out-competed the solution-phase primer, then the immobilized product would lack a sequencing primer binding site, and would result in an empty picotiter plate (PTP) well. If the CHR out-competed the bead-bound primer, the sequencing primer would still be present, and the only effect would be a shorter insert. Neither result would unduly compromise the sequencing quality. Given the large amount of genomic material used in the sample preparation process (currently 25 μg, containing $5.29 \times 10^{16}$ copies of the 35 Kb Adenovirus genome), oversampling can be used to provide fragments that lack the complete CHR, and allow standard PCR amplification of the region in question.

Breaking the Emulsion and Bead Recovery

Following amplification of the nucleic acid template and the attachment of amplification copies to the bead, the emulsion is "broken" (also referred to as "demulsification" in the art). There are many methods of breaking an emulsion (see, e.g., U.S. Pat. No. 5,989,892 and references cited therein) and one of skill in the art would be able to select an appropriate method. In the present invention, one preferred method of breaking the emulsion uses additional oil to cause the emulsion to separate into two phases. The oil phase is then removed, and a suitable organic solvent (e.g., hexanes) is added. After mixing, the oil/organic solvent phase is removed. This step may be repeated several times. Finally, the aqueous layers above the beads are removed. The beads are then washed with a mixture of an organic solvent and annealing buffer (e.g., one suitable annealing buffer is described in the examples), and then washed again in annealing buffer. Suitable organic solvents include alcohols such as methanol, ethanol, and the like.

The beads bound to amplification products may then be resuspended in aqueous solution for use, for example, in a sequencing reaction according to known technologies. (See, Sanger, F. et al., Proc. Natl. Acad. Sci. U.S.A. 75, 5463-5467 (1977); Maxam, A. M. & Gilbert, W. Proc Natl Acad Sci USA 74, 560-564 (1977); Ronaghi, M. et al., Science 281, 363, 365 (1998); Lysov, I. et al., Dokl Akad Nauk SSSR 303, 1508-1511 (1988); Bains W. & Smith G. C. J. Theor Biol 135, 303-307(1988); Dmanac, R. et al., Genomics 4, 114-128 (1989); Khrapko, K. R. et al., FEBS Lett 256. 118-122 (1989); Pevzner P. A. J Biomol Struct Dyn 7, 63-73 (1989); Southern, E. M. et al., Genomics 13, 1008-1017 (1992).)

If the beads are to be used in a pyrophosphate-based sequencing reaction (described, e.g., in U.S. Pat. Nos. 6,274,320, 6258,568 and 6,210,891, and incorporated in toto herein by reference), then it is necessary to remove the second strand of the PCR product and anneal a sequencing primer to the single stranded template that is bound to the bead. The second strand may be melted away using any number of commonly known methods such as addition of NaOH, application of low ionic (e.g., salt) strength, enzymatic degradation or displacement of the second strand, or heat processing. Following this strand removal step, the beads are pelleted and the supernatant is discarded. The beads are resuspended in an annealing buffer, and a sequencing primer or other non-amplification primer is added. The primer is annealed to the single stranded amplification product. This can be accomplished by using an appropriate annealing buffer and temperature conditions, e.g., as according to standard procedures in the art.

Purifying the Beads

At this point, the amplified nucleic acid on the bead may be sequenced either directly on the bead or in a different reaction vessel. In an embodiment of the present invention, the nucleic acid is sequenced directly on the bead by transferring the bead to a reaction vessel and subjecting the nucleic acid to a sequencing reaction (e.g., pyrophosphate or Sanger sequencing). Alternatively, the beads may be isolated and the nucleic acid may be removed from each bead and sequenced. In either case, the sequencing steps may be performed on each individual bead. However, this method, while commercially viable and technically feasible, may not be most effective because many of the beads will be "negative" (i.e., beads without amplified nucleic acid attached). In such cases, the optional process outlined below may be used to remove negative beads prior to distribution onto multiwell (e.g., picotiter) plates.

A high percentage of the beads may be negative if the goal is to minimize the number of beads that are associated with two or more different species of nucleic acid templates. For optimal pyrophosphate sequencing, each bead should contain multiple copies of a single species of nucleic acid. This can be achieved by maximizing the total number of beads combined with a single fragment of nucleic acid before amplification. For example, the following mathematical model can be used.

For the general case of N number of DNAs randomly distributed with M number of beads, the relative bead population associated with any number of DNAs depends on the ratio of N/M. The fraction of beads associated with N DNAs R(N) may be calculated using the Poisson distribution:

$R(N)=\exp-(N/M) \times (N/M)^N/N!$ (where x is the multiplication symbol)

Table 2, below, shows some calculated values for various N/M (the average DNA fragment-to-bead ratio) and N (the number of fragments associated with a bead).

TABLE 2

| N/M | 0.1 | 0.5 | 1 | 2 |
|---|---|---|---|---|
| R(0) | 0.9 | 0.61 | 0.37 | 0.13 |
| R(1) | 0.09 | 0.3 | 0.37 | 0.27 |
| R(N > 1) | 0.005 | 0.09 | 0.26 | 0.59 |

In Table 2, the top row denotes the various ratios of N/M. R(0) denotes the fraction of beads with no DNA, R(1) denotes the fraction of beads with one DNA (before amplification), and R(N>1) denotes the fraction of DNA with more than one DNA (before amplification).

Table 2 indicates that the maximum fraction of beads associated with a single DNA fragment is 0.37 (37%) and this occurs at a fragment-to-bead ratio of one-to-one. In this mixture, about 63% of the beads cannot be used for sequencing because they are associated with no DNA or they are associated with more than one species of DNA. However, controlling the fragment-to-bead ratio requires complex calculations, and variability can produce bead batches with a significantly smaller fraction of useable beads.

This inefficiency can be significantly ameliorated if beads containing amplicon (originating from the association with at least one fragment) are separated from those without amplicon (originating from beads with no associated fragments). An amplicon is defined as any nucleic acid molecules produced by an in vitro nucleic amplification technique. To increase efficiency, binding can be performed using low fragment-to-bead ratios (N/M<1). This minimizes the number of beads associated with more than one DNA. A separation step can be used to remove most or all of the beads with no DNA, leaving an enriched population of beads with one or more species of amplified DNA. This enriched population may be analyzed by any method of sequencing such as, for example, pyrophosphate sequencing. Because the fraction of beads with one amplicon (N=1) is enriched, any method of sequencing can be applied more efficiently.

As an example, with an average fragment-to-bead ratio of 0.1, 90% of the beads will carry no amplicon, 9% of the beads will carry one amplicon, and 0.5% of the beads will carry more than one amplicon. The enrichment described herein below will remove the 90% of the zero amplicon beads leaving a population of beads where the fraction available for sequencing (N=1) is:

1−(0.005/0.09)=94%.

Dilution of the fragment to bead mixture, along with separation of beads containing amplicon can yield an enrichment of 2.5 fold over the optimal unenriched method. For example, 94%/37% (See Table 2, above, N/M=1)=2.5. An additional benefit of the enrichment procedure described herein below is that the ultimate fraction of beads useful for sequencing is relatively insensitive to variability in N/M. Thus, complex calculations to derive the optimal N/M ratio are either unnecessary or may be performed with lower levels of precision. Accordingly, the methods of the invention can be easily adapted for use by less trained personnel or automation. An additional benefit of these methods is that the zero amplicon beads may be recycled and reused. While recycling is not necessary, it may reduce cost or the total bulk of reagents making the method of the invention more suitable for some purposes such as, for example, portable sampling, remote robotic sampling, and the like. In addition, the collective benefits of the disclosed methods (e.g., adaptation for less trained personnel, automation, and recycling of reagents) will reduce the costs of the methods. The enrichment procedure is described in more detail below.

The enrichment procedure may be used to treat beads that have been amplified in the bead emulsion method described above. The amplification is designed so that each amplified nucleic acid molecule contains the same sequence at its 3' end. The nucleotide sequence may be a 20 mer but may be any sequence from 15 bases or more such as 25 bases, 30 bases, 35 bases, 40 bases, or longer. While longer oligonucleotide ends are functional, they are not necessary. This 3' sequence may be introduced at the end of an amplified nucleic acid by one of skill in the art. For example, if PCR is used for amplification of a DNA template, the sequence may be included as part of one member of the PCR primer pair.

Figure 3:
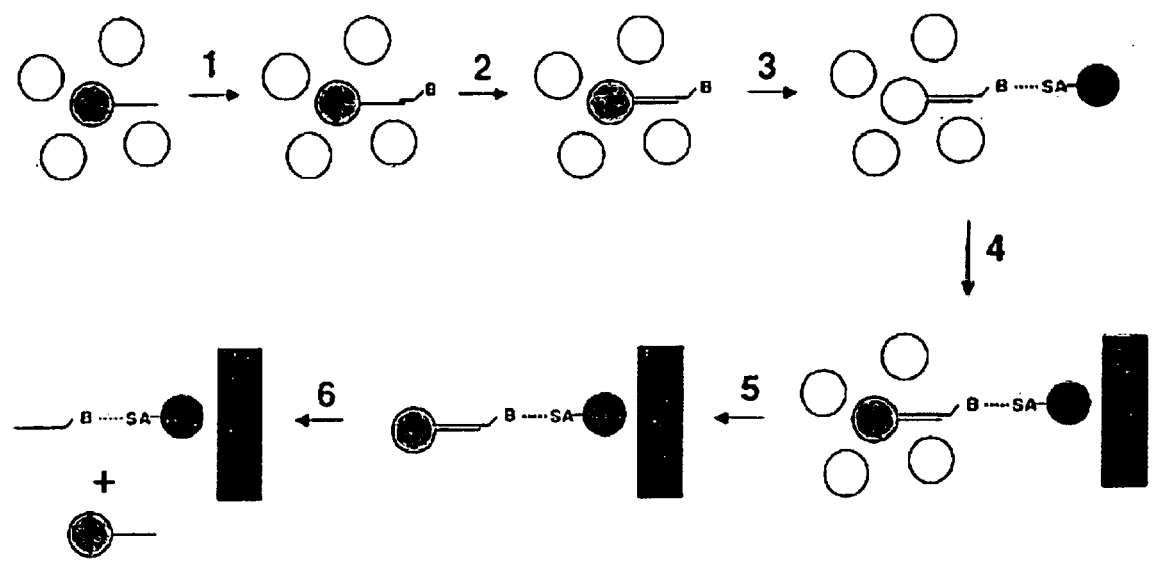
FIG. 3 Schematic of an enrichment process to remove beads that do not have any DNA attached thereto.

A schematic of the enrichment process is depicted in FIG. 3. In this process, the amplicon-bound bead is mixed with four empty beads to create a fragment-diluted amplification bead mixture. In step 1, a biotinylated primer complementary to the 3' end of the amplicon is annealed to the amplicon. In step 2, DNA polymerase and the four natural deoxynucleotide triphosphates (dNTPs) are added to the bead mixture and the biotinylated primer is extended. This extension is to enhance the bonding between the biotinylated primer and the bead-bound DNA. This step may be omitted if the biotinylated primer—DNA bond is strong (e.g., in a high ionic environment). In Step 3, streptavidin coated beads susceptible to attraction by a magnetic field (referred to herein as "magnetic streptavidin beads") are introduced to the bead mixtures. Magnetic beads are commercially available, for example, from Dynal (M290). The streptavidin capture moieties binds biotin groups hybridized to the amplicons, thereby binding the amplicon-bound beads to the magnetic streptavidin beads.

In step 5, a magnetic field (represented by a magnet) is applied near the reaction mixture, which causes the magnetic streptavidin beads/amplicon bound bead complexes to be positioned along one side of the tube most proximal to the magnetic field. Magnetic beads without amplicon bound beads attached are also expected to be positioned along the same side. Beads without amplicons remain in solution. The bead mixture is washed and the beads not bound by the magnet (i.e., the empty beads) are removed and discarded. In step 6, the extended biotinylated primer strand is separated from the amplicon strand by "melting." This step that can be accomplished, for example, by heat or a change in pH. The heat may be 60° C. in low salt conditions (e.g., in a low ionic environment such as 0.1×SSC). The change in pH may be accomplished by the addition of NaOH. Next, the mixture is washed and the supernatant containing the amplicon bound beads is recovered, while the magnetic beads are retained by a magnetic field. The resultant enriched beads may be used for DNA sequencing. It is noted that the primer on the DNA capture bead may be the same as the primer of step 2, above. In this case, annealing of the amplicon-primer complementary strands (with or without extension) is the source of target-capture affinity.

The biotin streptavidin pair could be replaced by a variety of capture-target pairs. For example, capture-target pairs can employ reversible (e.g., cleavable) or irreversible linkages. Non-limiting examples of reversible linkages include thiol-thiol, digoxigenin/anti-digoxigenin, and linkages using VEC-TREX® Avidin DLA (Vector Laboratories, Burlingame, Calif.), CaptAvidin™, NeutrAvidin™, and D-desthiobiotin (Molecular Probes, Inc., Eugene, Oreg.).

As described above, step 2 of the enrichment process is optional. If step 2 is omitted, it may not be necessary to separate the magnetic beads from the amplicon bound beads. The amplicon bound beads, with the magnetic beads attached, may be used directly for sequencing. For example, separation may not be necessary if sequencing is to be performed in a microtiter or picotiter plate and the amplicon bound bead-magnetic bead complex can fit inside the well of the plate.

While the use of magnetic capture beads is convenient, capture moieties can encompass other binding surfaces. For example, streptavidin can be chemically bound to a surface such as the inner surface of a tube. In this case, the amplified bead mixture may be flowed through the tube. The amplicon bound beads will tend to be retained until "melting" while the empty beads will flow through. This arrangement may be particularly advantageous for automating the bead preparation process.

While the embodiments described above are particularly useful, other methods to separate beads can be envisioned. For example, the capture beads may be labeled with a fluorescent moiety which would make the target-capture bead complex fluorescent. The target capture bead complex may be separated by flow cytometry or fluorescence cell sorter. Using large capture beads would allow separation by filtering or other particle size separation techniques. Since both capture and target beads are capable of forming complexes with a number of other beads, it is possible to agglutinate a mass of cross-linked capture-target beads. The large size of the agglutinated mass would make separation possible by simply washing away the unagglutinated empty beads. These methods described are described in more detail, for example, in Bauer, J.; J. Chromatography B, 722 (1999) 55-69 and in Brody et al., Applied Physics Lett. 74 (1999) 144-146.

In one embodiment, the invention encompasses a method for amplifying one or more nucleic acids comprising the steps of: a) forming a water-in-oil emulsion to create a plurality of aqueous microreactors wherein at least one of the microreactors comprises a single nucleic acid template, a single bead capable of binding to the nucleic acid, and amplification reaction solution containing reagents necessary to perform nucleic acid amplification; b) amplifying the nucleic acids in the microreactors to form amplified copies of the nucleic acids; and c) binding the amplified copies to the beads in the microreactors.

The amplification reaction solution used with this method may be a polymerase chain reaction solution comprising nucleotide triphosphates, a thermostable polymerase, and nucleic acid primers suspended in a buffer compatible with polymerase chain reaction conditions. The polymerase chain reaction is may be an asymmetric polymerase chain reaction or a symmetric polymerase chain reaction. As examples, amplification may be carried out by transcription-based amplification, rapid amplification of cDNA ends, continuous flow amplification, or rolling circle amplification.

For use with this method, a majority of the microreactors may include a single nucleic acid. The method may be performed with at least 10,000 nucleic acids, or at least 50,000 nucleic acids. Each bead used with the method can be used to capture more than 10,000 amplification copies of a nucleic acid template. In various embodiments, the emulsion additionally contains emulsion stabilizers. The emulsion stabilizers may be Atlox 4912, Span 80, or combinations or mixtures thereof. The emulsion may be heat stable, e.g., to 95° C., and may be formed by the dropwise addition of the nucleic acid templates, beads, and amplification reaction solution into an oil. The microreactors may have an average size of 50 to 250 µm in diameter.

In another embodiment, the invention encompasses a library comprising a plurality of nucleic acid molecules, wherein each nucleic acid molecule is separately immobilized to a different bead, and wherein each bead comprises over 1,000,000 clonal amplification copies of each nucleic acid molecule, wherein the library is contained in a single vessel. As examples, the nucleic acid molecules may be genomic DNA, cDNA, episomal DNA, BAC DNA, or YAC DNA. The genomic DNA may be animal, plant, viral, bacterial, or fungal genomic DNA. Preferably, the genomic DNA is human genomic DNA or human cDNA. In certain aspects, the bead, e.g., a Sepharose bead, has a diameter of 2 microns to 100 microns.

The invention also encompasses a method for amplifying a nucleic acid comprising the steps of: a) providing a nucleic acid template to be amplified; b) providing a solid support material comprising a generally spherical bead having a diameter about 10 to about 80 m, wherein the bead is capable of binding to the nucleic acid template; c) mixing the nucleic acid template and the bead in an amplification reaction solution containing reagents necessary to perform a nucleic acid amplification reaction in a water-in-oil emulsion; d) amplifying the nucleic acid template to form amplified copies of the nucleic acid template; and e) binding the amplified copies to the bead.

As an option, the method can include an enrichment step to isolate beads which bind amplified copies of the nucleic acid away from beads to which no nucleic acid is bound. This enrichment step may be performed by electrophoresis, cell sorting, or affinity purification (e.g., with magnetic beads that bind nucleic acid). Preferably, at least 100,000 copies of each target nucleic acid molecule are bound to each bead, at least 1,000,000 copies of each target nucleic acid molecule are bound to each bead, or at least 1 to 20,000,000 copies of each target nucleic acid molecule are bound to each bead. In various aspects, the beads are Sepharose beads and amplified copies are bound to the beads by a binding pair such as antigen/antibody, ligand/receptor, polyhistidine/nickel, or avidin/biotin. The method can also include the steps of: f) separating the template carrying beads and magnetic bead; and g) removing the magnetic beads with a magnetic field. This separation may be achieved by incubation at a temperature greater than 45° C. or by incubating the template carrying beads' and the magnetic beads in a solution with a basic pH.

The invention further encompasses a kit for conducting nucleic acid amplification of a nucleic acid template comprising: a) a nucleic acid capture bead; b) an emulsion oil; c) one or more emulsion stabilizers; and d) instructions for employing the kit.

Additionally, the invention encompasses a method for producing a clonal population of nucleic acids, comprising: a) providing a plurality of nucleic acid templates from 50-800 bp in length and beads capable of binding to the nucleic acid templates; b) mixing the nucleic acid templates and the beads in a biological reaction solution containing reagents necessary to amplify the nucleic acid templates; and c) forming an emulsion to create a plurality of microreactors comprising the nucleic acid templates, beads, and biological reaction solution, wherein at least one of the microreactors comprises a single nucleic acid template and a single bead encapsulated in the biological reaction solution, wherein the microreactors are contained in the same vessel.

In accordance with this method, the nucleic acids can be transcribed and translated to generate at least 10,000 copies of an expression product. The expression product may be bound to the beads by a binding pair selected from the group consisting of antigen/antibody, ligand/receptor, 6×his/nickel-nitrilotriacetic acid, and FLAG tag/FLAG antibody binding pairs. In certain aspects, the method produces a clonal population of proteins, such as antibodies, antibodies fragments, and engineered antibodies. The emulsion may comprise a plurality of thermostable microreactors, wherein the microreactors are 50 to 200 μm in diameter and comprise a biological reaction solution. The biological reaction solution may comprise reagents for performing polymerase chain reaction amplification reactions or coupled transcription and translation reactions. Preferably, a plurality of microreactors comprise a nucleic acid template, e.g., one or fewer nucleic acid templates, and one or fewer beads that bind to the nucleic acid templates.

EXAMPLES

Bead Emulsion PCR

The following procedures, including capture of the template DNA, DNA amplification, and recovery of the beads bound to amplified template, can be performed in a single tube. The emulsion format ensures the physical separation of the beads into 100-200 μm "microreactors" within this single tube, thus allowing for clonal amplification of the various templates. Mobilization of the amplification product is achieved through extension of the template along the oligonucleotides bound to the DNA capture beads. Typical, the copy number of the immobilized template ranges from 10 to 30 million copies per bead. The DNA capture beads affixed with multiple copies of a single species of nucleic acid template are ready for distribution onto PTPs.

The 300,000 75-picoliter wells etched in the PTP surface provide a unique array for the sequencing of short DNA templates in a massively parallel, efficient and cost-effective manner. However, this requires fairly large quantities (millions of copies) of clonal templates in each reaction well. The methods of the invention allow the user to clonally amplify single-stranded genomic template species thorough PCR reactions conducted in standard tubes or microtiter plates. Single copies of the template species may be mixed with capture beads, resuspended into complete PCR amplification solution, and emulsified into microreactors (100 to 200 μm in diameter), after which PCR amplification generates $10^7$-fold amplification of the initial template species. This procedure is much simpler and more cost-effective than previous methods.

Example 1

Binding Nucleic Acid Template to Capture Beads

This example describes preparation of a population of beads that preferably have only one unique nucleic acid template attached thereto. Successful clonal amplification depends on the delivery of a controlled number of template species (0.5 to 1) to each bead. Delivery of excess species can result in PCR amplification of a mixed template population, preventing generation of meaningful sequence data while a deficiency of species will result in fewer wells containing template for sequencing. This can reduce the extent of genome coverage provided by the sequencing phase. As a result, it is preferred that the template concentration be accurately determined through replicated quantitation, and that the binding protocol be followed as outlined below.

Template Quality Control

The success of the Emulsion PCR reaction is related to the quality of the template species. Regardless of the care and detail paid to the amplification phase, poor quality templates will impede successful amplification and the generation of meaningful sequence data. To prevent unnecessary loss of time and money, it is important to check the quality of the template material before initiating the Emulsion PCR phase of the process. Preferably, the library should pass two quality control steps before it is used in Emulsion PCR. Its concentration and the distribution of products it contains should be determined. Ideally, the library should appear as a heterogeneous population of fragments with little or no visible adapter dimers (e.g., ~90 bases). Also, amplification with PCR primers should result in a product smear ranging, for example, from 300 to 500 bp. Absence of amplification product may reflect failure to properly ligate the adaptors to the template, while the presence of a single band of any size may reflect contamination of the template.

Preparation of the PCR solution

The main consideration for this phase is to prevent contamination of the PCR reaction mixture with stray amplicons. Contamination of the PCR reactions with a residual amplicon is one of the critical issues that can cause failure of a sequencing run. To reduce the possibility of contamination, proper lab technique should be followed, and reaction mixture preparation should be conducted in a clean room in a UV-treated laminar flow hood.

PCR Reaction Mix:

For 200 μl PCR reaction mixture (enough for amplifying 600,000 beads), the following reagents were combined in a 0.2 ml PCR tube:

TABLE 3

|  | Stock | Final | Microliters |
|---|---|---|---|
| HIFI Buffer | 10 X | 1 X | 20 |
| treated nucleotides | 10 mM | 1 mM | 20 |
| Mg | 50 mM | 2 mM | 8 |
| BSA | 10% | 0.1% | 2 |
| Tween 80 | 1% | 0.01% | 2 |
| Ppase | 2 U | 0.003 U | 0.333333 |
| Primer MMP1a | 100 µM | 0.625 µM | 1.25 |
| Primer MMP1b | 10 µM | 0.078 µM | 1.56 |
| Taq polymerase | 5 U | 0.2 U | 8 |
| Water |  |  | 136.6 |
| Total |  |  | 200 |

The tube was vortexed thoroughly and stored on ice until the beads are annealed with template.

DNA Capture Beads:

1. 600,000 DNA capture beads were transferred from the stock tube to a 1.5 ml microfuge tube. The exact amount used will depend on bead concentration of formalized reagent.

2. The beads were pelleted in a benchtop mini centrifuge and supernatant was removed.

3. Steps 4-11 were performed in a PCR Clean Room.

4. The beads were washed with 1 mL of 1× Annealing Buffer.

5. The capture beads were pelleted in the microcentrifuge. The tube was turned 180° and spun again.

6. All but approximately 10 µl of the supernatant was removed from the tube containing the beads. The beads were not disturbed.

7. 1 mL of 1× Annealing Buffer was added and this mixture was incubated for 1 minute. The beads were then pelleted as in step 5.

8. All but approximately 100 µL of the material from the tube was removed.

9. The remaining beads and solution were transferred to a PCR tube.

10. The 1.5 mL tube was washed with 150 µL of 1× Annealing Buffer by pipetting up and down several times. This was added to the PCR tube containing the beads.

11. The beads were pelleted as in step 5 and all but 10 µL of supernatant was removed, taking care to not disturb the bead pellet.

12. An aliquot of quantitated single-stranded template DNA (sstDNA) was removed. The final concentration was 200,000-sst DNA molecules/µl.

13. 3 µl of the diluted sstDNA was added to PCR tube containing the beads. This was equivalent to 600,000 copies of sstDNA.

14. The tube was vortexed gently to mix contents.

15. The sstDNA was annealed to the capture beads in a PCR thermocycler with the program 80 Anneal stored in the EPCR folder on the M J Thermocycler, using the following protocol:

5 minutes at 65° C.;
 Decrease by 0.1° C./sec to 60° C.;
 Hold at 60° C. for 1 minute;
 Decrease by 0.1° C./sec to 50° C.;
 Hold at 50° C. for 1 minute;
 Decrease by 0.1° C./sec to 40° C.;
 Hold at 40° C. for 1 minute;
 Decrease by 0.1° C./sec to 20° C.; and
 Hold at 10° C. until ready for next step.

In most cases, beads were used for amplification immediately after template binding. If beads were not used immediately, they should were stored in the template solution at 4° C. until needed. After storage, the beads were treated as follows.

16. As in step 6, the beads were removed from the thermocycler, centrifuged, and annealing buffer was removed without disturbing the beads.

17. The beads were stored in an ice bucket until emulsification (Example 2).

18. The capture beads included, on average, 0.5 to 1 copies of sstDNA bound to each bead, and were ready for emulsification.

Example 2

Emulsification

This example describes how to create a heat-stable water-in-oil emulsion containing about 3,000 PCR microreactors per microliter. Outlined below is a protocol for preparing the emulsion.

1. 200 µl of PCR solution was added to the 600,000 beads (both components from Example 1).

2. The solution was pipetted up and down several times to resuspend the beads.

3. The PCR-bead mixture was allowed to incubate at room temperature for 2 minutes to equilibrate the beads with PCR solution.

4. 400 µl of Emulsion Oil was added to a UV-irradiated 2 ml microfuge tube.

5. An "amplicon-free" ¼" stir magnetic stir bar was added to the tube of Emulsion Oil.

An amplicon-free stir bar was prepared as follows. A large stir bar was used to hold a ¼" stir bar. The stir bar was then:
 Washed with DNA-Off (drip or spray);
 Rinsed with picopure water;
 Dried with a Kimwipe edge; and
 UV irradiated for 5 minutes.

6. The magnetic insert of a Dynal MPC-S tube holder was removed. The tube of Emulsion Oil was placed in the tube holder. The tube was set in the center of a stir plate set at 600 rpm.

7. The tube was vortexed extensively to resuspend the beads. This ensured that there was minimal clumping of beads.

8. Using a P-200 pipette, the PCR-bead mixture was added drop-wise to the spinning oil at a rate of about one drop every 2 seconds, allowing each drop to sink to the level of the magnetic stir bar and become emulsified before adding the next drop. The solution turned into a homogeneous milky white liquid with a viscosity similar to mayonnaise.

9. Once the entire PCR-bead mixture was been added, the microfuge tube was flicked a few times to mix any oil at the surface with the milky emulsion.

10. Stirring was continued for another 5 minutes.

11. Steps 9 and 10 were repeated.

12. The stir bar was removed from the emulsified material by dragging it out of the tube with a larger stir bar.

13. 10 µL of the emulsion was removed and placed on a microscope slide. The emulsion was covered with a cover slip and the emulsion was inspected at 50× magnification (10× ocular and 5× objective lens). A "good" emulsion was expected to include primarily single beads in isolated droplets (microreactors) of PCR solution in oil.

14. A suitable emulsion oil mixture with emulsion stabilizers was made as follows. The components for the emulsion mixture are shown in Table 4.

TABLE 4

| Ingredient | Quantity Required | Source | Ref. Number |
| --- | --- | --- | --- |
| Sigma Light Mineral Oil | 94.5 g | Sigma | M-5904 |
| Atlox 4912 | 1 g | Uniqema | NA |
| Span 80 | 4.5 g | Uniqema | NA |

The emulsion oil mixture was made by prewarming the Atlox 4912 to 60° C. in a water bath. Then, 4.5 grams of Span 80 was added to 94.5 grams of mineral oil to form a mixture. Then, one gram of the prewarmed Atlox 4912 was added to the mixture. The solutions were placed in a closed container and mixed by shaking and inversion. Any sign that the Atlox was settling or solidifying was remedied by warming the mixture to 60° C., followed by additional shaking.

Example 3

Amplification

This example describes amplification of the template DNA in the bead—emulsion mixture. According to this protocol of the invention, the DNA amplification phase of the process takes 3 to 4 hours. After the amplification is complete, the emulsion may be left on the thermocycler for up to 12 hours before beginning the process of isolating the beads. PCR thermocycling was performed by placing 50 to 100 µl of the emulsified reaction mixture into individual PCR reaction chambers (i.e., PCR tubes). PCR was performed as follows:

1. The emulsion was transferred in 50-100 µL amounts into approximately 10 separate PCR tubes or a 96-well plate using a single pipette tip. For this step, the water-in-oil emulsion was highly viscous.
2. The plate was sealed, or the PCR tube lids were closed, and the containers were placed into in a MJ thermocycler with or without a 96-well plate adaptor.
3. The PCR thermocycler was programmed to run the following program:
   1 cycle (4 minutes at 94° C.)—Hotstart Initiation;
   40 cycles (30 seconds at 94° C., 30 seconds at 58° C., 90 seconds at 68° C.);
   25 cycles (30 seconds at 94° C., 6 minutes at 58° C.); and
   Storage at 14° C.
4. After completion of the PCR reaction, the amplified material was removed in order to proceed with breaking the emulsion and bead recovery.

Example 4

Breaking the Emulsion and Bead Recovery

This example describes how to break the emulsion and recover the beads with amplified template thereon. Preferably, the post-PCR emulsion should remain intact. The lower phase of the emulsion should, by visual inspection, remain a milky white suspension. If the solution is clear, the emulsion may have partially resolved into its aqueous and oil phases, and it is likely that many of the beads will have a mixture of templates. If the emulsion has broken in one or two of the tubes, these samples should not be combined with the others. If the emulsion has broken in all of the tubes, the procedure should not be continued.

1. All PCR reactions from the original 600 µl sample were combined into a single 1.5 ml microfuge tube using a single pipette tip. As indicated above, the emulsion was quite viscous. In some cases, pipetting was repeated several times for each tube. As much material as possible was transferred to the 1.5 ml tube.
2. The remaining emulsified material was recovered from each PCR tube by adding 50 µl of Sigma Mineral Oil into each sample. Using a single pipette tip, each tube was pipetted up and down a few times to resuspend the remaining material.
3. This material was added to the 1.5 ml tube containing the bulk of the emulsified material.
4. The sample was vortexed for 30 seconds.
5. The sample was spun for 20 minutes in the tabletop microfuge tube at 13.2K rpm in the Eppendorf microcentrifuge.
6. The emulsion separated into two phases with a large white interface. As much of the top, clear oil phase as possible was removed. The cloudy material was left in the tube. Often a white layer separated the oil and aqueous layers. Beads were often observed pelleted at the bottom of the tube.
7. The aqueous layer above the beads was removed and saved for analysis (gel analysis, Agilent 2100, and Taqman). If an interface of white material persisted above the aqueous layer, 20 microliters of the underlying aqueous layer was removed. This was performed by penetrating the interface material with a pipette tip and withdrawing the solution from underneath.
8. In the PTP Fabrication and Surface Chemistry Room Fume Hood, 1 ml of Hexanes was added to the remainder of the emulsion.
9. The sample was vortexed for 1 minute and spun at full speed for 1 minute.
10. In the PTP Fabrication and Surface Chemistry Room Fume Hood, the top, oil/hexane phase was removed and placed into the organic waste container.
11. 1 ml of 1× Annealing Buffer was added in 80% Ethanol to the remaining aqueous phase, interface, and beads.
12. The sample was vortexed for 1 minute or until the white substance dissolved.
13. The sample was centrifuged for 1 minute at high speed. The tube was rotated 180 degrees, and spun again for 1 minute. The supernatant was removed without disturbing the bead pellet.
14. The beads were washed with 1 ml of 1× Annealing Buffer containing 0.1% Tween 20 and this step was repeated.

Example 5

Single Strand Removal and Primer Annealing

If the beads are to be used in a pyrophosphate-based sequencing reaction, then it is necessary to remove the second strand of the PCR product and anneal a sequencing primer to the single stranded template that is bound to the bead. This example describes a protocol for accomplishing that.

1. The beads were washed with 1 ml of water, and spun twice for 1 minute. The tube was rotated 180° between spins. After spinning, the aqueous phase was removed.
2. The beads were washed with 1 ml of 1 mM EDTA. The tube was spun as in step 1 and the aqueous phase was removed.
3. 1 ml of 0.125 M NaOH was added and the sample was incubated for 8 minutes.
4. The sample was vortexed briefly and placed in a microcentrifuge.

5. After 6 minutes, the beads were pelleted as in step 1 and as much solution as possible was removed.

6. At the completion of the 8 minute NaOH incubation, 1 ml of 1× Annealing Buffer was added.

7. The sample was briefly vortexed, and the beads were pelleted as in step 1. As much supernatant as possible was removed, and another 1 ml of 1× Annealing buffer was added.

8. The sample was briefly vortexed, the beads were pelleted as in step 1, and 800 µl of 1× Annealing Buffer was removed.

9. The beads were transferred to a 0.2 ml PCR tube.

10. The beads were transferred and as much Annealing Buffer as possible was removed, without disturbing the beads.

11. 100 µl of 1× Annealing Buffer was added.

12. 4 µl of 100 µM sequencing primer was added. The sample was vortexed just prior to annealing.

13. Annealing was performed in a MJ thermocycler using the "80 Anneal" program.

14. The beads were washed three times with 200 µl of 1× Annealing Buffer and resuspended with 100 µl of 1× Annealing Buffer.

15. The beads were counted in a Hausser Hemacytometer. Typically, 300,000 to 500,000 beads were recovered (3,000-5,000 beads/µL).

16. Beads were stored at 4° C. and could be used for sequencing for 1 week.

Example 6

Optional Enrichment Step

The beads may be enriched for amplicon containing bead using the following procedure. Enrichment is not necessary but it could be used to make subsequent molecular biology techniques, such as DNA sequencing, more efficient.

Fifty microliters of 10 µM (total 500 pmoles) of biotin-sequencing primer was added to the Sepharose beads containing amplicons from Example 5. The beads were placed in a thermocycler. The primer was annealed to the DNA on the bead by the thermocycler annealing program of Example 2.

After annealing, the sepharose beads were washed three times with Annealing Buffer containing 0.1% Tween 20. The beads, now containing ssDNA fragments annealed with biotin-sequencing primers, were concentrated by centrifugation and resuspended in 200 µl of BST binding buffer. Ten microliters of 50,000 unit/ml Bst-polymerase was added to the resuspended beads and the vessel holding the beads was placed on a rotator for five minutes. Two microliters of 10 mM dNTP mixture (i.e., 2.5 µl each of 10 mM dATP, dGTP, dCTP and dTTP) was added and the mixture was incubated for an additional 10 minutes at room temperature. The beads were washed three times with annealing buffer containing 0.1% Tween 20 and resuspended in the original volume of annealing buffer.

Fifty microliters of Dynal Streptavidin beads (Dynal Biotech Inc., Lake Success, N.Y.; M270 or MyOne™ beads at 10 mg/ml) was washed three times with Annealing Buffer containing 0.1% Tween 20 and resuspended in the original volume in Annealing Buffer containing 0.1% Tween 20. Then the Dynal bead mixture was added to the resuspended sepharose beads. The mixture was vortexed and placed in a rotator for 10 minutes at room temperature.

The beads were collected on the bottom of the test tube by centrifugation at 2300 g (500 rpm for Eppendorf Centrifuge 5415D). The beads were resuspended in the original volume of Annealing Buffer containing 0.1% Tween 20. The mixture, in a test tube, was placed in a magnetic separator (Dynal). The beads were washed three times with Annealing Buffer containing 0.1% Tween 20 and resuspended in the original volume in the same buffer. The beads without amplicons were removed by wash steps, as previously described. Only Sepharose beads containing the appropriated DNA fragments were retained.

The magnetic beads were separated from the sepharose beads by addition of 500 µl of 0.125 M NaOH. The mixture was vortexed and the magnetic beads were removed by magnetic separation. The Sepharose beads remaining in solution was transferred to another tube and washed with 400 µl of 50 mM Tris Acetate until the pH was stabilized at 7.6.

Example 7

Nucleic Acid Sequencing Using Bead Emulsion PCR

The following experiment was performed to test the efficacy of the bead emulsion PCR. For this protocol, 600,000 Sepharose beads, with an average diameter of 25-35 µm (as supplied my the manufacturer) were covalently attached to capture primers at a ratio of 30-50 million copies per bead. The beads with covalently attached capture primers were mixed with 1.2 million copies of single stranded Adenovirus Library. The library constructs included a sequence that was complimentary to the capture primer on the beads.

The adenovirus library was annealed to the beads using the procedure described in Example 1. Then, the beads were resuspended in complete PCR solution. The PCR Solution and beads were emulsified in 2 volumes of spinning emulsification oil using the same procedure described in Example 2. The emulsified (encapsulated) beads were subjected to amplification by PCR as outlined in Example 3. The emulsion was broken as outlined in Example 4. DNA on beads was rendered single stranded, sequencing primer was annealed using the procedure of Example 5.

Next, 70,000 beads were sequenced simultaneously by pyrophosphate sequencing using a pyrophosphate sequencer from 454 Life Sciences (New Haven, Conn.) (see copending application of Lohman et al., filed concurrently herewith entitled Methods of Amplifying and Sequencing Nucleic Acids" U.S. Ser. No. 60/476,592 filed Jun. 6, 2003). Multiple batches of 70,000 beads were sequenced and the data were listed in Table 5, below.

TABLE 5

| Alignment Error | Alignments | | | | | |
|---|---|---|---|---|---|---|
| Tolerance | None | Single | Multiple | Unique | Coverage | Inferred Read Error |
| 0% | 47916 | 1560 | | 1110 | 54.98% | 0.00% |
| 5% | 46026 | 3450 | | 2357 | 83.16% | 1.88% |
| 10% | 43474 | 6001 | 1 | 3742 | 95.64% | 4.36% |

Table 5 shows the results obtained from BLAST analysis comparing the sequences obtained from the pyrophosphate sequencer against Adenovirus sequence. The first column shows the error tolerance used in the BLAST program. The last column shows the real error as determined by direct comparison to the known sequence.

Bead Emulsion PCR for Doubled Ended Sequencing

Example 8

Template Quality Control

As indicated previously, the success of the Emulsion PCR reaction was found to be related to the quality of the single stranded template species. Accordingly, the quality of the template material was assessed with two separate quality controls before initiating the Emulsion PCR protocol. First, an aliquot of the single-stranded template was run on the 2100 BioAnalyzer (Agilent). An RNA Pico Chip was used to verify that the sample included a heterogeneous population of fragments, ranging in size from approximately 200 to 500 bases. Second, the library was quantitated using the RiboGreen fluorescence assay on a Bio-Tek FL600 plate fluorometer. Samples determined to have DNA concentrations below 5 ng/µl were deemed too dilute for use.

Example 9

DNA Capture Bead Synthesis

Packed beads from a 1 mL N-hydroxysuccinimide ester (NHS)-activated Sepharose HP affinity column (Amersham Biosciences, Piscataway, N.J.) were removed from the column. The 30-25 µm size beads were selected by serial passage through 30 and 25 µm pore filter mesh sections (Sefar America, Depew, N.Y., USA). Beads that passed through the first filter, but were retained by the second were collected and activated as described in the product literature (Amersham Pharmacia Protocol # 71700600AP). Two different amine-labeled HEG (hexaethyleneglycol) long capture primers were obtained, corresponding to the 5' end of the sense and anti-sense strand of the template to be amplified, (5'-Amine-3 HEG spacers gcttacctgaccgacctctgcctatcccctgttgcgtgtc-3'; SEQ ID NO:1; and 5'-Amine-3 HEG spacers ccattc-cccagctcgtcttgccatctgttccctccctgtc-3'; SEQ ID NO:2) (IDT Technologies, Coralville, Iowa, USA). The primers were designed to capture of both strands of the amplification products to allow double ended sequencing, i.e., sequencing the first and second strands of the amplification products. The capture primers were dissolved in 20 mM phosphate buffer, pH 8.0, to obtain a final concentration of 1 mM. Three microliters of each primer were bound to the sieved 30-25 µm beads. The beads were then stored in a bead storage buffer (50 mM Tris, 0.02% Tween and 0.02% sodium azide, pH 8). The beads were quantitated with a hemacytometer (Hausser Scientific, Horsham, Pa., USA) and stored at 4° C. until needed.

Example 10

PCR Reaction Mix Preparation and Formulation

As with any single molecule amplification technique, contamination of the reactions with foreign or residual amplicon from other experiments could interfere with a sequencing run. To reduce the possibility of contamination, the PCR reaction mix was prepared in a in a UV-treated laminar flow hood located in a PCR clean room. For each 600,000 bead emulsion PCR reaction, the following reagents were mixed in a 1.5 ml tube: 225 µl of reaction mixture (1× Platinum HiFi Buffer (Invitrogen)), 1 mM dNTPs, 2.5 mM $MgSO_4$ (Invitrogen), 0.1% BSA, 0.01% Tween, 0.003 U/µl thermostable PPi-ase (NEB), 0.125 µM forward primer (5'-gcttacctgaccgacctctg-3'; SEQ ID NO:3) and 0.125 µM reverse primer (5'-ccattc-cccagctcgtcttg-3'; SEQ ID NO:4) (IDT Technologies, Coralville, Iowa, USA) and 0.2 U/µl Platinum Hi-Fi Taq Polymerase (Invitrogen). Twenty-five microliters of the reaction mixture was removed and stored in an individual 200 µl PCR tube for use as a negative control. Both the reaction mixture and negative controls were stored on ice until needed.

Example 11

Binding Template Species to DNA Capture Beads

Successful clonal DNA amplification for sequencing relates to the delivery of a controlled number of template species to each bead. For the experiments described herein below, the typical target template concentration was determined to be 0.5 template copies per capture bead. At this concentration, Poisson distribution dictates that 61% of the beads have no associated template, 30% have one species of template, and 9% have two or more template species. Delivery of excess species can result in the binding and subsequent amplification of a mixed population (2 or more species) on a single bead, preventing the generation of meaningful sequence data. However, delivery of too few species will result in fewer wells containing template (one species per bead), reducing the extent of sequencing coverage. Consequently, it was deemed that the single-stranded library template concentration was important.

Template nucleic acid molecules were annealed to complimentary primers on the DNA capture beads by the following method, conducted in a UV-treated laminar flow hood. Six hundred thousand DNA capture beads suspended in bead storage buffer (see Example 9, above) were transferred to a 200 µl PCR tube. The tube was centrifuged in a benchtop mini centrifuge for 10 seconds, rotated 180°, and spun for an additional 10 seconds to ensure even pellet formation. The supernatant was removed, and the beads were washed with 200 µl of Annealing Buffer (20 mM Tris, pH 7.5 and 5 mM magnesium acetate). The tube was vortexed for 5 seconds to resuspend the beads, and the beads were pelleted as before. All but approximately 10 µl of the supernatant above the beads was removed, and an additional 200 µl of Annealing Buffer was added. The beads were again vortexed for 5 seconds, allowed to sit for 1 minute, and then pelleted as before. All but 10 µl of supernatant was discarded.

Next, 1.5 µl of 300,000 molecules/µl template library was added to the beads. The tube was vortexed for 5 seconds to mix the contents, and the templates were annealed to the beads in a controlled denaturation/annealing program preformed in an MJ thermocycler. The program allowed incubation for 5 minutes at 80° C., followed by a decrease by 0.1° C./sec to 70° C., incubation for 1 minute at 70° C., decrease by 0.1° C./s 60° C., hold at 60° C. for 1 minute, decrease by 0.1° C./sec to 50° C., hold at 50° C. for 1 minute, decrease by 0.1° C./sec to 20° C., hold at 20° C. Following completion of the annealing process, the beads were removed from the thermocycler, centrifuged as before, and the Annealing Buffer was carefully decanted. The capture beads included on average 0.5 copy of single stranded template DNA bound to each bead, and were stored on ice until needed.

Example 12

Emulsification

The emulsification process creates a heat-stable water-in-oil emulsion containing 10,000 discrete PCR microreactors per microliter. This serves as a matrix for single molecule, clonal amplification of the individual molecules of the target library. The reaction mixture and DNA capture beads for a single reaction were emulsified in the following manner. In a UV-treated laminar flow hood, 200 µl of PCR solution (from Example 10) was added to the tube containing the 600,000 DNA capture beads (from Example 11). The beads were resuspended through repeated pipetting. After this, the PCR-bead mixture was incubated at room temperature for at least 2 minutes, allowing the beads to equilibrate with the PCR solution. At the same time, 450 µl of Emulsion Oil (4.5% (w:w) Span 80, 1% (w:w) Atlox 4912 (Uniqema, Del.) in light mineral oil (Sigma)) was aliquotted into a flat-topped 2 ml centrifuge tube (Dot Scientific) containing a sterile ¼ inch magnetic stir bar (Fischer). This tube was then placed in a custom-made plastic tube holding jig, which was then centered on a Fisher Isotemp digital stirring hotplate (Fisher Scientific) set to 450 RPM.

Figure 4:
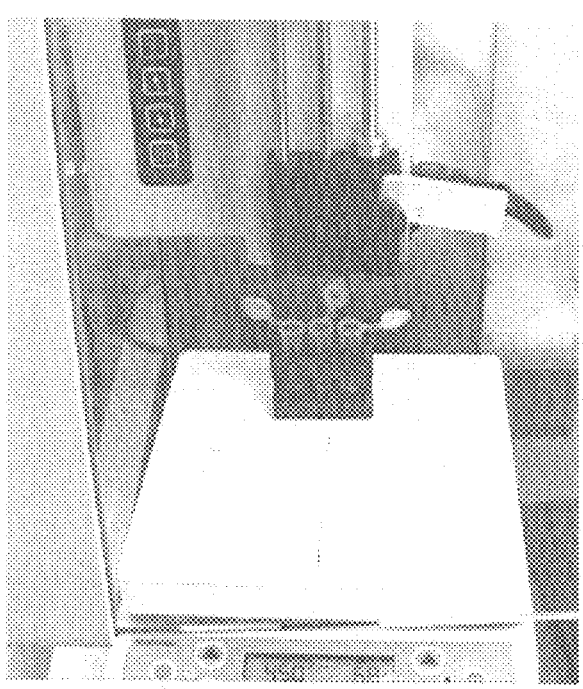
FIG. 4 Depiction of jig used to hold tubes on the stir plate below vertical syringe pump. The jig was modified to hold three sets of bead emulsion amplification reaction mixtures. The syringe was loaded with the PCR reaction mixture and beads.
Figure 5:
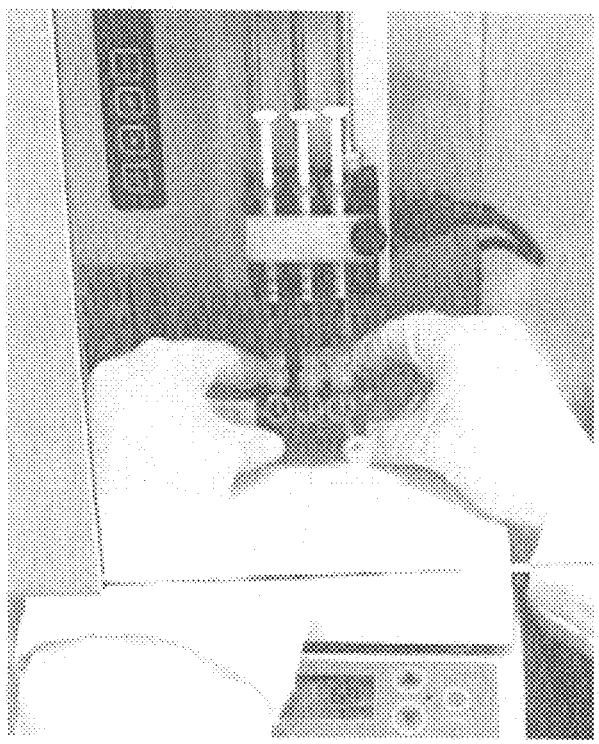
FIG. 5 Depiction of optimal placement of syringes in vertical syringe pump and orientation of emulsion tubes below syringe outlets.
Figure 6:
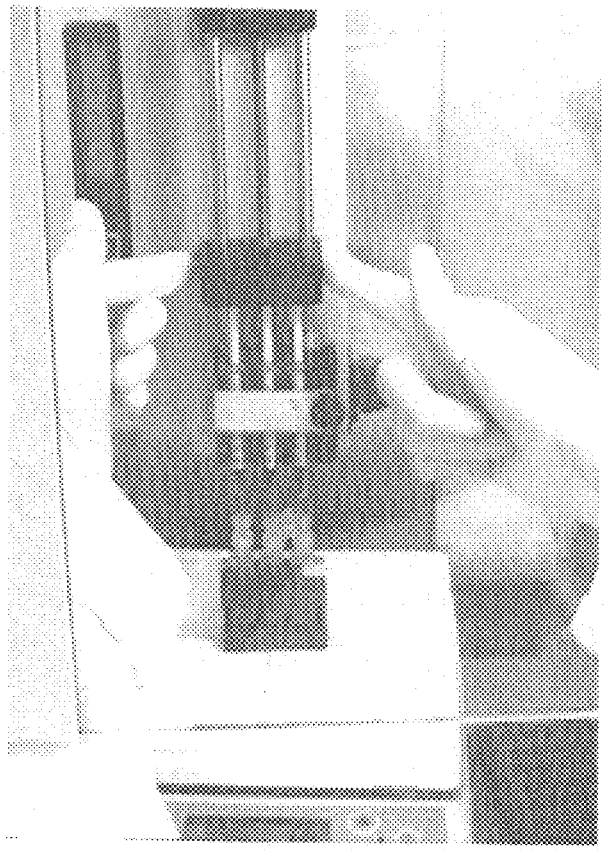
FIG. 6 Depiction of optimal placement of syringe pump pusher block against syringe plungers, and optimal orientation of jig on the stir plate. Using this arrangement, the syringe contents were expelled into the agitated emulsion oil.

The PCR-bead solution was vortexed for 15 seconds to resuspend the beads. The solution was then drawn into a 1 ml disposable plastic syringe (Benton-Dickenson) affixed with a plastic safety syringe needle (Henry Schein). The syringe was placed into a syringe pump (Cole-Parmer) modified with an aluminum base unit orienting the pump vertically rather than horizontally (e.g., FIGS. 4-6). The tube with the emulsion oil was aligned on the stir plate so that it was centered below the plastic syringe needle and the magnetic stir bar was spinning properly. The syringe pump was set to dispense 0.6 ml at 5.5 ml/hr. The PCR-bead solution was added to the emulsion oil in a dropwise fashion. Care was taken to ensure that the droplets did not contact the side of the tube as they fell into the spinning oil.

Once the emulsion was formed, great care was taken to minimize agitation of the emulsion during both the emulsification process and the post-emulsification aliquotting steps. It was found that vortexing, rapid pipetting, or excessive mixing could cause the emulsion to break, destroying the discrete microreactors. In forming the emulsion, the two solutions turned into a homogeneous milky white mixture with the viscosity of mayonnaise. The contents of the syringe were emptied into the spinning oil. Then, the emulsion tube was removed from the holding jig, and gently flicked with a forefinger until any residual oil layer at the top of the emulsion disappeared. The tube was replaced in the holding jig, and stirred with the magnetic stir bar for an additional minute. The stir bar was removed from the emulsion by running a magnetic retrieval tool along the outside of the tube, and the stir bar was discarded.

Figure 7:
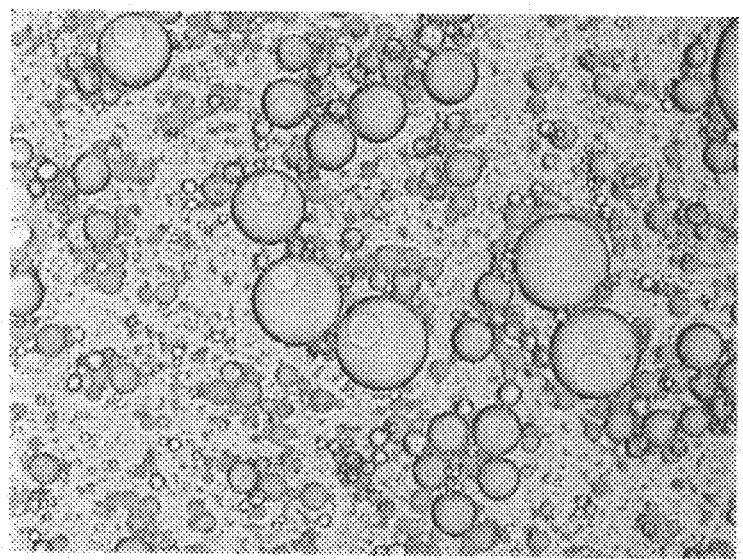
FIG. 7 Depiction of beads (see arrows) suspended in individual microreactors according to the methods of the invention.
Figure 8:
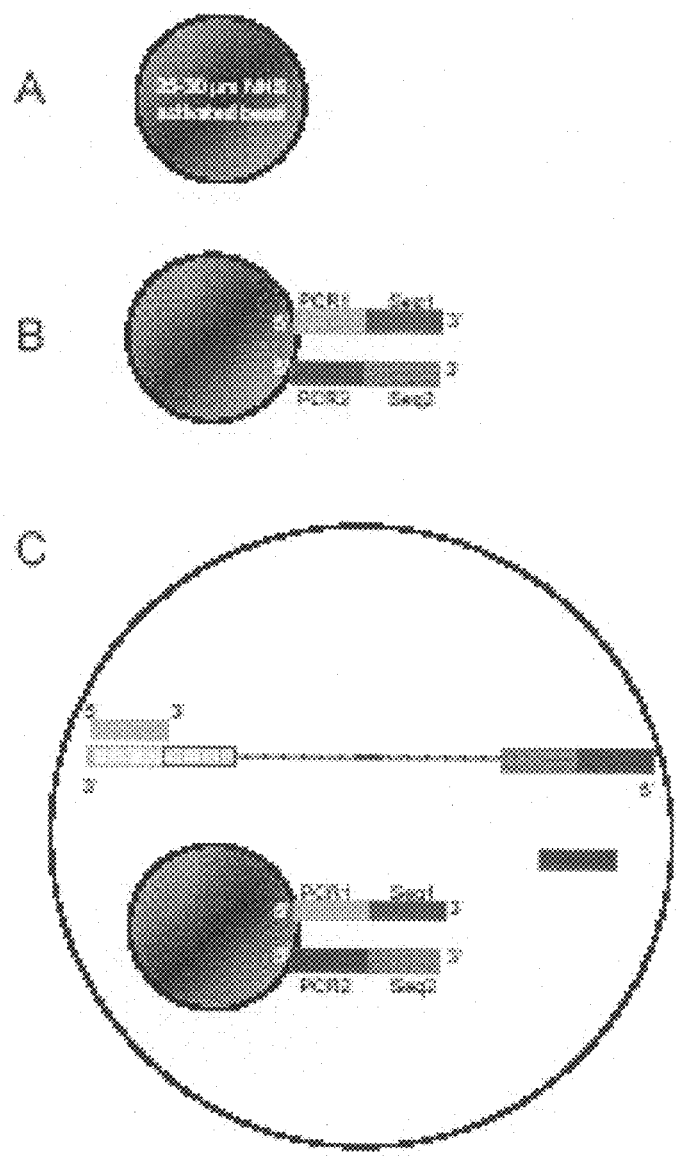
FIGS. 8A-8C Schematic showing the initial stages of bead emulsion amplification used in conjunction with double ended sequencing. The NHS-activated bead (FIG. 8A) is attached with capture primers (FIG. 8B), and encapsulated in a microreactor comprising the DNA capture bead and template (FIG. 8C).
Figure 9:
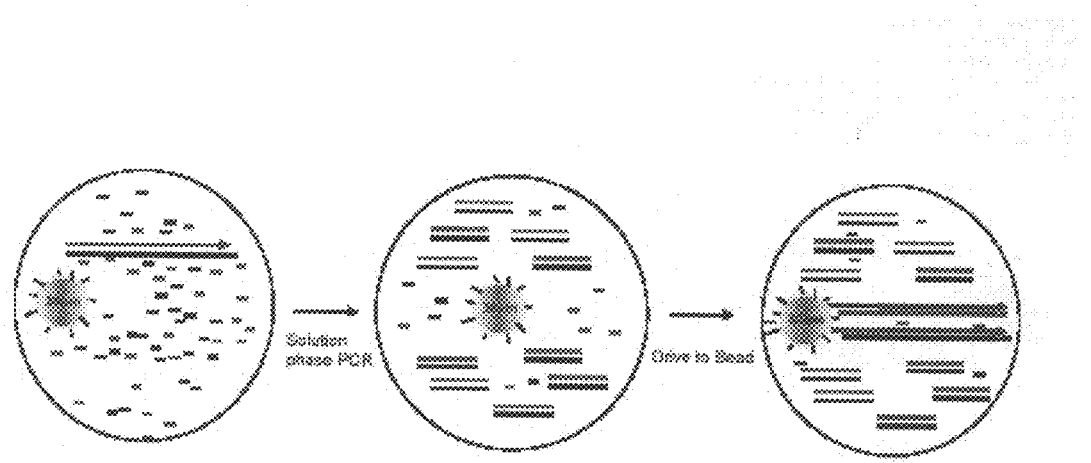
FIG. 9 Schematic showing the amplification and capture stages of bead emulsion amplification used in conjunction with double ended sequencing. The template is amplified by solution phase PCR and the amplification products are attached to the DNA capture bead.
Figure 10:
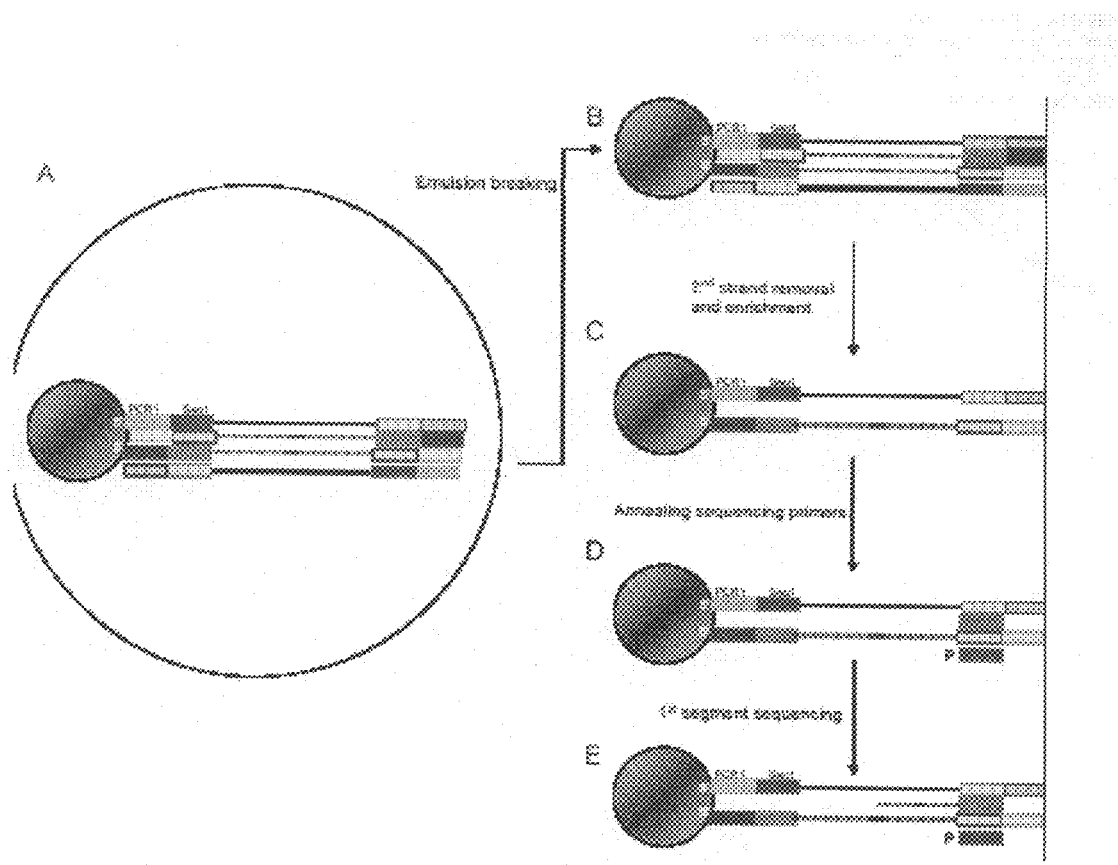
FIG. 10 Schematic showing the later stages of bead emulsion amplification used in conjunction with double ended sequencing. The emulsion is broken down (FIGS. 10A-10B), the second strand of the amplification product is removed and enrichment is used to maximize the number of beads bound with amplification product (FIG. 10C), the sequencing primers are annealed (FIG. 10D), and the first strand is sequenced (FIG. 10E), followed by the second strand.

Twenty microliters of the emulsion was taken from the middle of the tube using a P100 pipettor and placed on a microscope slide. The larger pipette tips were used to minimize shear forces. The emulsion was inspected at 50× magnification to ensure that it was comprised predominantly of single beads in 30 to 150 micron diameter microreactors of PCR solution in oil (FIG. 7). After visual examination, the emulsions were immediately amplified.

Example 13

Amplification

The emulsion was aliquotted into 7-8 separate PCR tubes. Each tube included approximately 75 µl of the emulsion. The tubes were sealed and placed in a MJ thermocycler along with the 25 µl negative control described above. The following cycle times were used: 1 cycle of incubation for 4 minutes at 94° C. (Hotstart Initiation), 30 cycles of incubation for 30 seconds at 94° C., and 150 seconds at 68° C. (Amplification), and 40 cycles of incubation for 30 seconds at 94° C., and 360 seconds at 68° C. (Hybridization and Extension). After completion of the PCR program, the tubes were removed and the emulsions were broken immediately or the reactions were stored at 10° C. for up to 16 hours prior to initiating the breaking process.

Example 14

Breaking the Emulsion and Bead Recovery

Following amplification, the emulstifications were examined for breakage (separation of the oil and water phases). Unbroken emulsions were combined into a single 1.5 ml microcentrifuge tube, while the occasional broken emulsion was discarded. As the emulsion samples were quite viscous, significant amounts remained in each PCR tube. The emulsion remaining in the tubes was recovered by adding 75 µl of mineral oil into each PCR tube and pipetting the mixture. This mixture was added to the 1.5 ml tube containing the bulk of the emulsified material. The 1.5 ml tube was then vortexed for 30 seconds. After this, the tube was centrifuged for 20 minutes in the benchtop microcentrifuge at 13.2K rpm (full speed).

After centrifugation, the emulsion separated into two phases with a large white interface. The clear, upper oil phase was discarded, while the cloudy interface material was left in the tube. In a chemical fume hood, 1 ml hexanes was added to the lower phase and interface layer. The mixture was vortexed for 1 minute and centrifuged at full speed for 1 minute in a benchtop microcentrifuge. The top, oil/hexane phase was removed and discarded. After this, 1 ml of 80% Ethanol/1× Annealing Buffer was added to the remaining aqueous phase, interface, and beads. This mixture was vortexed for 1 minute or until the white material from the interface was dissolved. The sample was then centrifuged in a benchtop microcentrifuge for 1 minute at full speed. The tube was rotated 180 degrees, and spun again for an additional minute. The supernatant was then carefully removed without disturbing the bead pellet.

The white bead pellet was washed twice with 1 ml Annealing Buffer containing 0.1% Tween 20. The wash solution was discarded and the beads were pelleted after each wash as described above. The pellet was washed with 1 ml Picopure water. The beads were pelleted with the centrifuge-rotate-centrifuge method used previously. The aqueous phase was carefully removed. The beads were then washed with 1 ml of 1 mM EDTA as before, except that the beads were briefly vortexed at a medium setting for 2 seconds prior to pelleting and supernatant removal.

Amplified DNA, immobilized on the capture beads, was treated to obtain single stranded DNA. The second strand was removed by incubation in a basic melt solution. One ml of Melt Solution (0.125 M NaOH, 0.2 M NaCl) was subsequently added to the beads. The pellet was resuspended by vortexing at a medium setting for 2 seconds, and the tube placed in a Thermolyne LabQuake tube roller for 3 minutes. The beads were then pelleted as above, and the supernatant was carefully removed and discarded. The residual Melt solution was neutralized by the addition of 1 ml Annealing Buffer. After this, the beads were vortexed at medium speed for 2 seconds. The beads were pelleted, and the supernatant was removed as before. The Annealing Buffer wash was repeated, except that only 800 µl of the Annealing Buffer was removed after centrifugation. The beads and remaining Annealing Buffer were transferred to a 0.2 ml PCR tube. The beads were used immediately or stored at 4° C. for up to 48 hours before continuing on to the enrichment process.

Example 15

Bead Enrichment

The bead mass included beads with amplified, immobilized DNA strands, and empty or null beads. As mentioned previously, it was calculated that 61% of the beads lacked template DNA during the amplification process. Enrichment was used to selectively isolate beads with template DNA, thereby maximizing sequencing efficiency. The enrichment process is described in detail below.

The single stranded beads from Example 14 were pelleted with the centrifuge-rotate-centrifuge method, and as much supernatant as possible was removed without disturbing the beads. Fifteen microliters of Annealing Buffer were added to the beads, followed by 2 µl of 100 µM biotinylated, 40 base enrichment primer (5'-Biotin-tetra-ethyleneglycol spacers ccattccccagctcgtcttgccatctgttccctccctgtctcag-3'; SEQ ID NO:5). The primer was complimentary to the combined amplification and sequencing sites (each 20 bases in length) on the 3' end of the bead-immobilized template. The solution was mixed by vortexing at a medium setting for 2 seconds, and the enrichment primers were annealed to the immobilized DNA strands using a controlled denaturation/annealing program in an MJ thermocycler. The program consisted of the following cycle times and temperatures: incubation for 30 seconds at 65° C., decrease by 0.1° C./sec to 58° C., incubation for 90 seconds at 58° C., and hold at 10° C.

While the primers were annealing, Dynal MyOne™ streptavidin beads were resuspend by gentle swirling. Next, 20 µl of the MyOne™ beads were added to a 1.5 ml microcentrifuge tube containing 1 ml of Enhancing fluid (2 M NaCl, 10 mM Tris-HCl, 1 mM EDTA, pH 7.5). The MyOne bead mixture was vortexed for 5 seconds, and the tube was placed in a Dynal MPC-S magnet. The paramagnetic beads were pelleted against the side of the microcentrifuge tube. The supernatant was carefully removed and discarded without disturbing the MyOne™ beads. The tube was removed from the magnet, and 100 µl of enhancing fluid was added. The tube was vortexed for 3 seconds to resuspend the beads, and stored on ice until needed.

Upon completion of the annealing program, 100 µl of annealing buffer was added to the PCR tube containing the DNA capture beads and enrichment primer. The tube vortexed for 5 seconds, and the contents were transferred to a fresh 1.5 ml microcentrifuge tube. The PCR tube in which the enrichment primer was annealed to the capture beads was washed once with 200 µl of annealing buffer, and the wash solution was added to the 1.5 ml tube. The beads were washed three times with 1 ml of annealing buffer, vortexed for 2 seconds, and pelleted as before. The supernatant was carefully removed. After the third wash, the beads were washed twice with 1 ml of ice cold Enhancing fluid. The beads were vortexed, pelleted, and the supernatant was removed as before. The beads were resuspended in 150 µl ice cold Enhancing fluid and the bead solution was added to the washed MyOne™ beads.

The bead mixture was vortexed for 3 seconds and incubated at room temperature for 3 minutes on a LabQuake tube roller. The streptavidin-coated MyOne™ beads were bound to the biotinylated enrichment primers annealed to immobilized templates on the DNA capture beads. The beads were then centrifuged at 2,000 RPM for 3 minutes, after which the beads were vortexed with 2 second pulses until resuspended. The resuspended beads were placed on ice for 5 minutes. Following this, 500 µl of cold Enhancing fluid was added to the beads and the tube was inserted into a Dynal MPC-S magnet. The beads were left undisturbed for 60 seconds to allow pelleting against the magnet. After this, the supernatant with excess MyOne™ and null DNA capture beads was carefully removed and discarded.

The tube was removed from the MPC-S magnet, and 1 ml of cold enhancing fluid added to the beads. The beads were resuspended with gentle finger flicking. It was important not to vortex the beads at this time, as forceful mixing could break the link between the MyOne™ and DNA capture beads. The beads were returned to the magnet, and the supernatant removed. This wash was repeated three additional times to ensure removal of all null capture beads. To remove the annealed enrichment primers and MyOne™ beads, the DNA capture beads were resuspended in 400 µl of melting solution, vortexed for 5 seconds, and pelleted with the magnet. The supernatant with the enriched beads was transferred to a separate 1.5 ml microcentrifuge tube. For maximum recovery of the enriched beads, a second 400 µl aliquot of melting solution was added to the tube containing the MyOne™ beads. The beads were vortexed and pelleted as before. The supernatant from the second wash was removed and combined with the first bolus of enriched beads. The tube of spent MyOne™ beads was discarded.

The microcentrifuge tube of enriched DNA capture beads was placed on the Dynal MPC-S magnet to pellet any residual MyOne™ beads. The enriched beads in the supernatant were transferred to a second 1.5 ml microcentrifuge tube and centrifuged. The supernatant was removed, and the beads were washed 3 times with 1 ml of annealing buffer to neutralize the residual melting solution. After the third wash, 800 µl of the supernatant was removed, and the remaining beads and solution were transferred to a 0.2 ml PCR tube. The enriched beads were centrifuged at 2,000 RPM for 3 minutes and the supernatant decanted. Next, 20 µl of annealing buffer and 3 µl of two different 100 µM sequencing primers (5'-ccatctgttcctccctgtc-3'; SEQ ID NO:6; and 5'-cctatcccctgttgcgtgtc-3' phosphate; SEQ ID NO:7) were added. The tube was vortexed for 5 seconds, and placed in an MJ thermocycler for the following 4-stage annealing program: incubation for 5 minutes at 65° C., decrease by 0.1° C./sec to 50° C., incubation for 1 minute at 50° C., decrease by 0.1° C./sec to 40° C., hold at 40° C. for 1 minute, de 0.1° C./sec to 15° C., and hold at 15° C.

Upon completion of the annealing program, the beads were removed from thermocycler and pelleted by centrifugation for 10 seconds. The tube was rotated 180°, and spun for an additional 10 seconds. The supernatant was decanted and discarded, and 200 µl of annealing buffer was added to the tube. The beads were resuspended with a 5 second vortex, and pelleted as before. The supernatant was removed, and the beads resuspended in 100 µl annealing buffer. At this point, the beads were quantitated with a Multisizer 3 Coulter Counter (Beckman Coulter). Beads were stored at 4° C. and were stable for at least 1 week.

Throughout this specification, various patents, published patent applications and scientific references are cited to describe the state and content of the art. Those disclosures, in their entireties, are hereby incorporated into the present specification by reference.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims.

What is claimed is:

1. A method for amplifying one or more nucleic acids onto a bead comprising the steps of:
   (a) forming a water-in-oil emulsion to create a plurality of aqueous microreactors wherein a plurality of the microreactors comprises on average one single stranded nucleic acid template, a single bead with a first population comprising a plurality of molecules of a first primer species disposed thereon, and an amplification reaction solution comprising a second population comprising a plurality of molecules of the first primer species and a plurality of molecules of a second primer species and reagents necessary to perform nucleic acid amplification, wherein the first primer species is capable of binding to the single stranded nucleic acid template, the second primer species is capable of binding to a complementary strand of the single stranded nucleic acid template, and further wherein the molecules of the second primer species and the molecules of the first population of the primer species are each present in greater numbers within the aqueous microreactors than the number of molecules of the second population of the first primer species;
   (b) asymmetrically amplifying the single stranded nucleic acid template and the complementary strand to the template strand in the amplification reaction solution to form a population of amplified copies of the single stranded template nucleic acid, wherein substantially all of the molecules of the second population of the first primer species in the amplification reaction solution are depleted;
   (c) binding a plurality of the asymmetrically amplified copies of the single stranded template nucleic acid to the first population of the first primer species on the bead in a plurality of the microreactors, wherein at least 100,000 bead bound complementary strands are extended from the first primer species to form a population of beads with amplified nucleic acid template bound thereto;
   (d) breaking the emulsion to release the population of beads with amplified nucleic acid template bound thereto from the microreactors and away from the amplification reaction solution comprising unbound amplification products; and
   (e) enriching for beads with amplified nucleic acid template bound thereto by removing beads to which no nucleic acid is bound; and
   (f) distributing the beads with amplified nucleic acid template bound thereto onto an array.

2. The method of claim 1, wherein a majority of the microreactors include a single nucleic acid.

3. The method of claim 1, wherein said amplification reaction solution is a polymerase chain reaction solution further comprising nucleotide triphosphates, a thermostable polymerase, and a buffer compatible with polymerase chain reaction conditions.

4. The method of claim 1, wherein said emulsion additionally contains emulsion stabilizers.

5. The method of claim 4, wherein said emulsion stabilizers are selected from the group consisting of Atlox 4912, Span 80, and combinations and mixtures thereof.

6. The method of claim 1 wherein said emulsion is heat stable.

7. The method of claim 6 wherein said emulsion is heat stable to 95° C.

8. The method of claim 1, wherein amplification is carried out by a method selected from the group consisting of transcription-based amplification, rapid amplification of cDNA ends, continuous flow amplification, and rolling circle amplification.

9. The method of claim 1, wherein the emulsion is formed by the dropwise addition of the nucleic acid templates, beads, and amplification reaction solution into an oil.

10. The method of claim 1, performed with at least 10,000 nucleic acid templates.

11. The method of claim 1, performed with at least 50,000 nucleic acid templates.

12. The method of claim 1, wherein the microreactors have an average size of 50 μm.

13. The method of claim 1, wherein each bead binds more than 10,000 asymmetrically amplified copies of the single stranded nucleic acid template.

14. The method of claim 1, further comprising the step of:
   (g) sequencing the amplified nucleic acid templates.

15. The method of claim 1 wherein enrichment step (f) is performed using magnetic beads having primers attached thereto that bind the amplified nucleic acid template.

16. The method of claim 1, wherein at least 1,000,000 copies of each target nucleic acid molecule are bound to each bead.

17. The method of claim 1, wherein between at least 1 to 20,000,000 copies of each target nucleic acid molecule are bound to each bead.

18. The method of claim 1, wherein the beads are sepharose beads.

19. The method of claim 15, further comprising, after step (e), the step of:
separating the beads with amplified nucleic acid template thereon away from the magnetic beads.

20. The method of claim 19, wherein the separating is achieved by incubation at a temperature greater than 45° C. or by incubating the beads with amplified nucleic acid template thereon and the magnetic beads in a solution with a basic pH.

* * * * *

UNITED STATES PATENT AND TRADEMARK OFFICE
CERTIFICATE OF CORRECTION

| | | |
|---|---|---|
| PATENT NO. | : 7,842,457 B2 | Page 1 of 1 |
| APPLICATION NO. | : 10/767899 | |
| DATED | : November 30, 2010 | |
| INVENTOR(S) | : Jan Berka | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 427 days.

Signed and Sealed this
Ninth Day of August, 2011

David J. Kappos
*Director of the United States Patent and Trademark Office*